(12) United States Patent
Chatzistergos et al.

(10) Patent No.: US 10,786,536 B2
(45) Date of Patent: Sep. 29, 2020

(54) CARDIAC NEURAL CREST CELLS AND METHODS OF USE THEREOF

(71) Applicant: VESTION, INC., Miami, FL (US)

(72) Inventors: Konstantinos E. Chatzistergos, Miami, FL (US); Joshua M. Hare, Miami Beach, FL (US)

(73) Assignee: VESTION, INC., Miami, FL (US)

(*) Notice: Subject to any disclaimer, the term of this patent is extended or adjusted under 35 U.S.C. 154(b) by 104 days.

(21) Appl. No.: 15/032,965

(22) PCT Filed: Oct. 29, 2014

(86) PCT No.: PCT/US2014/062939
§ 371 (c)(1),
(2) Date: Apr. 28, 2016

(87) PCT Pub. No.: WO2015/066197
PCT Pub. Date: May 7, 2015

(65) Prior Publication Data
US 2016/0250261 A1    Sep. 1, 2016

Related U.S. Application Data

(60) Provisional application No. 61/896,945, filed on Oct. 29, 2013.

(51) Int. Cl.
| A61K 35/34 | (2015.01) |
| C12N 5/077 | (2010.01) |
| A61K 45/06 | (2006.01) |

(52) U.S. Cl.
CPC .............. *A61K 35/34* (2013.01); *A61K 45/06* (2013.01); *C12N 5/0657* (2013.01); *C12N 2500/25* (2013.01); *C12N 2500/38* (2013.01); *C12N 2501/155* (2013.01); *C12N 2501/235* (2013.01); *C12N 2501/40* (2013.01); *C12N 2501/999* (2013.01); *C12N 2502/1329* (2013.01); *C12N 2506/02* (2013.01); *C12N 2506/45* (2013.01); *C12N 2513/00* (2013.01)

(58) Field of Classification Search
CPC ...... A61K 35/34; A61K 45/06; C12N 5/0657; C12N 5/077; C12N 2500/25; C12N 2500/38; C12N 2502/1329; C12N 2501/155; C12N 2501/40; C12N 2501/999; C12N 2506/02; C12N 2513/00; C12N 2501/235; C12N 2506/45; A61P 9/00; A61P 25/00
See application file for complete search history.

(56) References Cited

U.S. PATENT DOCUMENTS

| 6,387,369 B1 | 5/2002 | Pittenger et al. |
| 6,930,222 B2 | 8/2005 | Yu |
| 7,070,943 B2 | 7/2006 | Darzynkiewicz et al. |
| 9,980,985 B2 | 5/2018 | Hare et al. |
| 2003/0054973 A1 | 3/2003 | Anversa |
| 2004/0126879 A1 | 7/2004 | Schneider et al. |
| 2006/0008450 A1 | 1/2006 | Verfaillie et al. |
| 2007/0005389 A1 | 1/2007 | Apparao et al. |
| 2007/0053839 A1 | 3/2007 | Zhang |
| 2007/0212676 A1 | 9/2007 | Takakura et al. |
| 2009/0162329 A1* | 6/2009 | Anversa ............ C12N 15/1137 424/93.7 |
| 2010/0166714 A1* | 7/2010 | Chien ................. C12N 5/0662 424/93.7 |
| 2010/0260727 A1 | 10/2010 | Hare et al. |
| 2011/0123500 A1 | 5/2011 | Anversa et al. |
| 2012/0034595 A1* | 2/2012 | Phillips ..................... A61P 9/00 435/3 |
| 2013/0280809 A1* | 10/2013 | Efe ....................... C12N 5/0678 435/467 |
| 2014/0162366 A1* | 6/2014 | Izpisua Belmonte ....................... C12N 5/0691 435/467 |
| 2014/0301991 A1* | 10/2014 | Srivastava ................. A61P 9/00 424/93.21 |
| 2014/0369976 A1 | 12/2014 | Hare et al. |
| 2015/0140658 A1* | 5/2015 | Kamp .................. C12N 5/0661 435/377 |
| 2015/0316535 A1 | 11/2015 | Hare et al. |

FOREIGN PATENT DOCUMENTS

| JP | 2013531497 A | 8/2013 |
| WO | WO2000/006701 A1 | 2/2000 |
| WO | 2005033298 A1 | 4/2005 |
| WO | WO2006/039630 A2 | 4/2006 |
| WO | WO2008/054819 A2 | 5/2008 |
| WO | WO2008/058216 A2 | 5/2008 |
| WO | 2011157029 A1 | 12/2011 |
| WO | WO2014/093051 A2 | 6/2014 |

OTHER PUBLICATIONS

Hao et al. (2008) Dorsomorphin, a selective small molecule inhibitor of BMP signaling, promotes cardiomyogenesis in embryonic stem cells. PLoS One 3(8):e2904.*
Wu et al. (2006) Developmental origin of a bipotential myocardial and smooth muscle cell precursor in the mammalian heart. Cell 127(6):1137-1150.*
Orlic et al., Nature, 410, Apr. 2001 (Year: 2001).*
Yuasa et al., Nature Biotechnology, 23(5): 607-611, May 2005 (Year: 2005).*
Mummery et al., Circ Res; 111:344-358, 2010 (Year: 2010).*
Beltrami et al., Adult Cardiac Stem Cells are Multipotent and Support Myocardial Regeneration, *Cell* (Sep. 19, 2003), (114) pp. 763-776.

(Continued)

*Primary Examiner* — Kimberly Ballard
*Assistant Examiner* — Stacey N Macfarlane
(74) *Attorney, Agent, or Firm* — Troutman Pepper Hamilton Sanders LLP

(57) ABSTRACT

Cardiac neural crest cells and methods for making and using the same to effect cardiac injury is described herein.

9 Claims, 24 Drawing Sheets

Specification includes a Sequence Listing.

(56) References Cited

OTHER PUBLICATIONS

Chatzistergos et al., "Abstract 18448: Ckit Marks Cardiac Neural Crest Progenitors in the Developing Mouse Heart," American Heart Association, Scientific Sessions and Resuscitation Science Symposium (2013), 128(22) pp. 1-20.
Dai et al., "Allogeneic Mesenchymal Stem Cell Transplantation in Postinfarcted Rat Myocardium Short- and Long-Term Effects," Circulation, Lippincott Williams & Wilkins, US (Jul. 12, 2005), 112(2) pp. 214-223.
Dingar et al., "Anti-apoptotic Function of the E2F Transcription Factor 4 (E2F4)/p130, a Member of Retinoblastoma Gene Family in Cardiac Myocytes", Journal of Molecular and Cellular Cardiology (Sep. 15, 2012), 53(6):820-828.
European Patent Office, "Extended European Search Report" by Examiner Damien Bochelen, dated Feb. 24, 2012, pp. 1-13.
European Patent Office, "Extended European Search Report" by Examiner N. Loubrdou-Bourges, dated Mar. 16, 2016, pp. 1-10.
Hatzistergos et al., "Bone Marrow Mesenchymal Stem Cells Stimulate Cardiac Stem Cell Proliferation and Differentiation", Circulation Research (Oct. 1, 2010), 107(7):913-922.
Hatzistergos et al., "Abstract 19546: Retinoblastoma Regulates Cardiac and Mesenchymal Stem Cell Niches during Adult Heart Regeneration," Circulation (Nov. 20, 2012), 126:A19546.
Hou et al., "Transplantation of mesenchymal stem cells from human bone marrow improves damaged heart function in rats," International Journal of Cardiology, Elsevier Science Publishers (Jan. 25, 2007) 115(2) pp. 220-228.
Huang et al., "Transplantation of angiogenin-overexpressing mesenchymal stem cells synergistically augments cardiac function in a porcine model of chronic ischemia," Journal of Thoracic and Cardiovascular Surgery, Mosby-Yearbook, Inc. (Nov. 29, 2006), 132(6) pp. 1329-1338.
International Search Report and Written Opinion for International Application No. PCT/US2013/072660 dated Jul. 1, 2014.
International Search Report and Written Opinion for International Application No. PCT/US2014/062939 dated Mar. 16, 2015.
Jiang et al., "Homing and differentiation of mesenchymal stem cells delivered intravenously to ischemic myocardium in vivo: a time-series study," Pflugers Archiv—European Journal of Physiology (Aug. 17, 2006), 453(1) pp. 43-52.
Li et al., "Bone marrow mesenchymal stem cells differentiate into cardiac phenotypes by cardiac microenvironment", Journal of Molecular and Cellular Cardiology, Academic Press, GB (Jan. 24, 2007), 42(2) pp. 295-303.
Sdek et al., "Assessment of Cardiomyocyte DNA Synthesis During Hypertrophy in Adult Mice", The Journal of Cell Biology: JCB (Aug. 8, 2011), 266(3):H1439-423.
Tamura et al., "Neural Crest-Derived Stem Cells Migrate and Differentiate Into Cardiomyocytes After Myocardial Infarction," Arterioscler Thromb Vasc Biol. (2011), 31(3) pp. 582-589.
Toma et al., "Human Mesenchymal Stem Cells Differentiate to a Cardiomyocyte Phenotype in the Adult Murine Heart," Circulation, Lippincott Williams & Wilkins (Jan. 8, 2002), 105(1) pp. 93-98.
Tomita et al., "Cardiac neural crest cells contribute to the dormant multipotent stem cell in the mammalian heart," J Cell Biology (2005), 170(7) pp. 1135-1146.
Uosaki et al., "Direct Contact with Endoderm-Like Cells Efficiently Induces Cardiac Progenitors from Mouse and Human Pluripotent Stem Cells", Plos One (Oct. 1, 2012), 7(10):e46413.
Wang et al., "The roles of mesenchymal stem cells (MSCs) therapy in ischemic heart diseases," Biochemical and Biophysical Research Communications, Academic Press Inc. (Jun. 9, 2007), 359(2) pp. 189-193.
Yang et al., "A Key Role for Telomerase Reverse Transcriptase Unit in Modulating Human Embryonic Stem Cells Proliferation, Cell Cycle Dynamics, and In Vitro Differentiation," Stem Cells (Jan. 17, 2008), 26(4) pp. 805-863.
Oskouei et al., Increased Potency of Cardiac Stem Cells Compared with Bone Marrow Mesenchymal Stem Cells in Cardiac Repair, Stem Cells Translational Medicine (Feb. 7, 2012), 1(2):116-124.
Enrichment of Pluripotent Stem Cell Derived Neural Crest Stem Cells and Further Differentiation to Peripheral Neurons, retrieved from https://www.miltenyibiotec.com/en/research-areas/stem-cell-research/es-and-ips-cells/~/media/Images/Products/Import/0007200/IM007298.ashx.
European Search Report and Written Opinion (Partial) for European Application No. 14858818.9 dated May 19, 2017.
Faucherre et al., The Heart's Content-renewalble Resources, Int'l J. of Cardiology (Oct. 6, 2012), 167(4):1141-1146.
Holmes et al., "Preparation of Cells and Reagents for Flow Cytometry," Current Protocols in Immun.(2001), Unit 5.3:1-24.
Lee et al., Derivation of Neural Crest Cells from Human Pluripotent Stem Cells, Nature Protocols, Nature Publishing Group, GB (Apr. 1, 2010), 5(4):688-701.
Medepalli et al., "A New Technique for Reversible permeabilization of live cells for intracellular delivery of quantum dots," Nanotech. (2013), 24(205101):1-13.
Practical Flow Cytometry (Shapiro, John Wiley & Sons) (Feb. 25, 2005), 43.
Lam et al. Embroyic stem cell-derived cardiomyocytes harbor a subpopulation of niche-forming Sco-1progenitor cells, Mol. Cell. Biochem (Dec. 3, 2010) 349(1-2):69-76.
Lin et al. High-purity enrichment of functional cardiovascular cells from human iPS cells, Cardio. Res. (Aug. 2012) 95(3):327-335.
Hatzistergos, "STNext Retinoblastoma Reulates Cardiac and Mesenchymal Stem Cell Niches during Adult Heart Regeneration" Circulation (Nov. 20, 2012) vol. 126, No. 21 Suppl. S, pp. 19546, http://corc.ahajournals.org.
Soonpaa et al., "Assessment of cardiomyocyte DNA synthesis during hypertrophy in adult mice", Am. J. Physiol. 266 (Heart Circ. Physiol. 35):(1994) H1439-H1445.
Tamura et al., "The review of basic studies about the cardiac stem cell and regenerative medicine," Nippon Rinsho (2008), 66 (5) pp. 908-914.
Williams et al., "Enhanced Effect of Human Cardiac Stem Cells and Bone Marrow Mesenchymal Stem Cells to Reduce Infarct Size and Restore Cardiac Function after Myocardial Infarction" NHIMS432077, Circulation (2013) 124(2): 213-223.
Nonfinal Office Action dated Dec. 2, 2019 received in U.S. Appl. No. 15/972,462.
Final Office Action dated Jan. 10, 2020 in U.S. Appl. No. 15/972,472.

\* cited by examiner

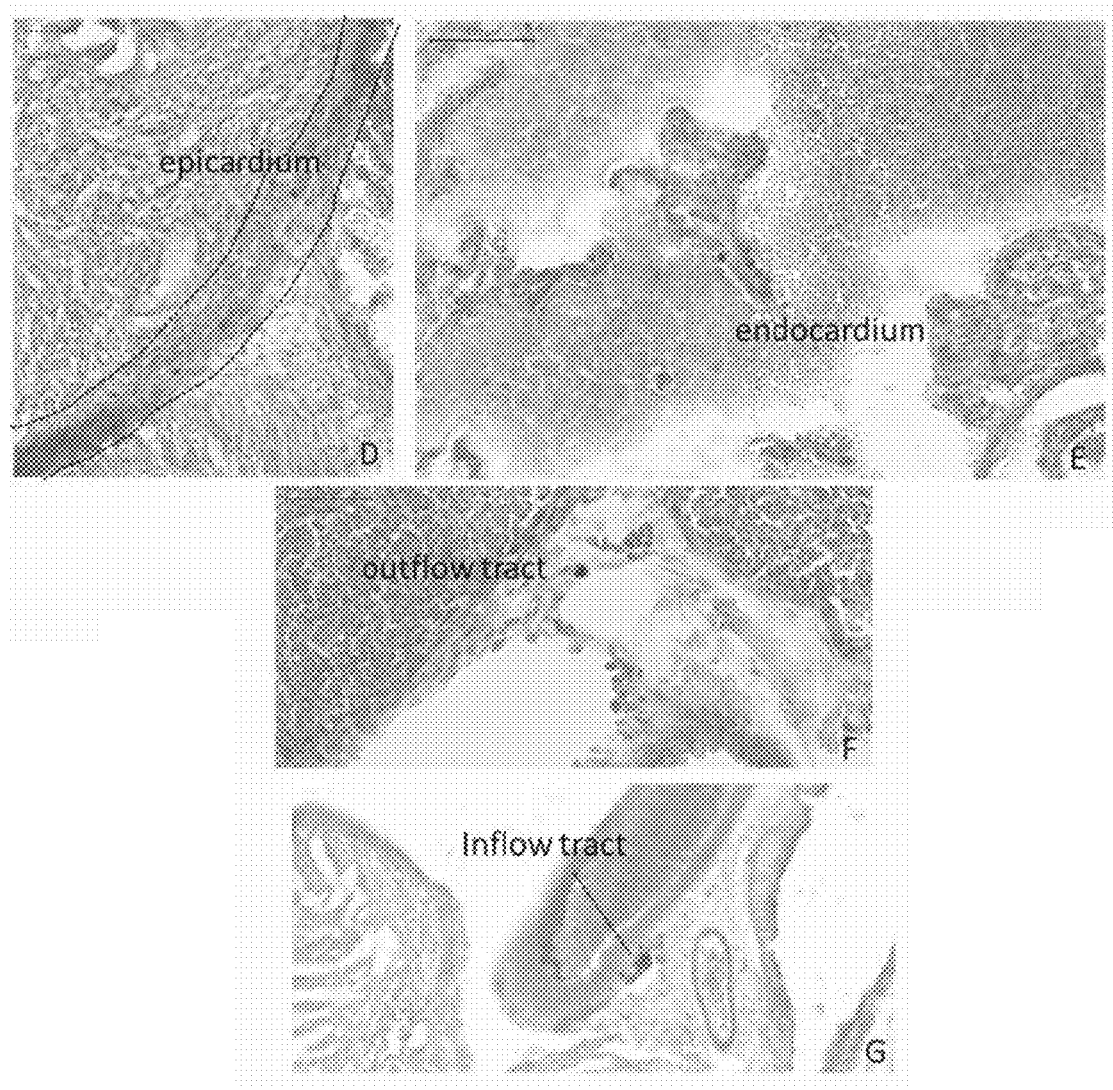
FIG. 14-Continued

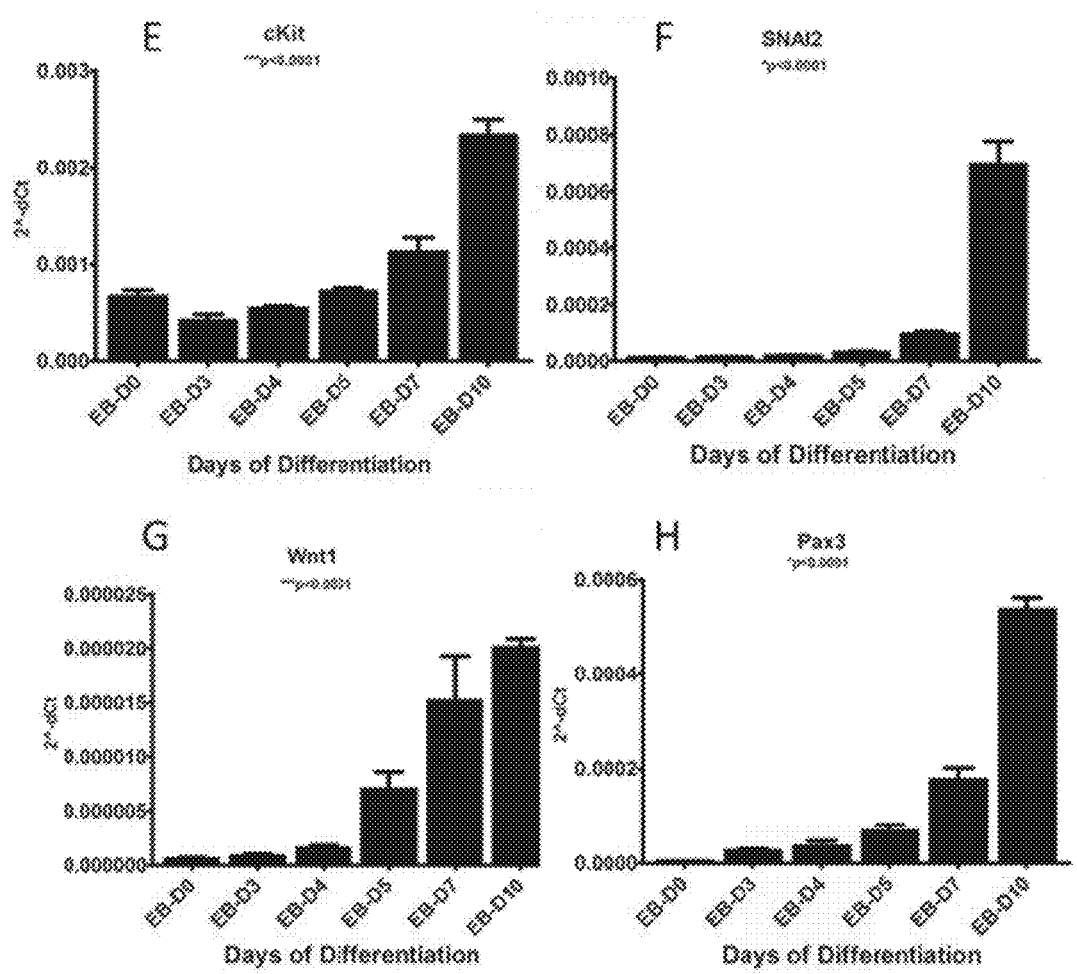
FIG. 18-Continued

CARDIAC NEURAL CREST CELLS AND METHODS OF USE THEREOF

CROSS-REFERENCE TO RELATED APPLICATIONS

This application is a U.S. national stage filing under 35 U.S.C. § 371 of International Application No. PCT/US2014/062939 entitled "Cardiac Neural Crest Cells And Methods Of Use Thereof," and filed on Oct. 29, 2014, which claims benefit of and priority under 35 U.S.C. § 119(e) to U.S. Provisional Application No. 61/896,945 entitled "Cardiac Neural Crest Cells," filed Oct. 29, 2013. The contents of each of these applications are incorporated herein by reference in their entireties.

BACKGROUND

Stem cells have been used to treat various heart disorders and conditions. However, there is a need to identify and use different types of stem cells. The present embodiments fulfill these needs and others.

BRIEF SUMMARY

Presently disclosed is a method for treating a cardiac injury in a subject in need thereof by administering a therapeutically effective amount of a pharmaceutical composition comprising cardiac neural crest cells. The method can include cardiac neural crest cells which are cKit positive. In some embodiments, the cardiac injury can be a cardiac injury caused by myocardial infarction, heart failure, cardiomyopathy, congenital heart disease, nutritional diseases, ischemic or non-ischemic cardiomyopathy, hypertensive cardiomyopathy, valvular cardiomyopathy, inflammatory cardiomyopathy, cardiomyopathy secondary to a systemic metabolic disease, alcoholic cardiomyopathy, diabetic cardiomyopathy, restrictive cardiomyopathy, and combinations thereof.

In some embodiments, the pharmaceutical composition can have about 50% by weight to about 100% by weight cardiac neural crest cells. In other embodiments, the pharmaceutical composition can have about 50% by weight cardiac neural crest cells, about 70% by weight cardiac neural crest cells, or about 90% by weight cardiac neural crest cells. In some embodiments, the pharmaceutical composition can have about $1 \times 10^6$ cardiac neural crest cells or about $1 \times 10^8$ cardiac neural crest cells.

In some embodiments, the pharmaceutical composition can have one or more differentiation agents. The one or more differentiation agents can be selected from BMP antagonist, noggin, chordin, Tsg, soluble receptors such as BMPR1A and BMPR1B, small molecule BMP antagonist such as dorsomorphin, retinoic acid receptor agonist such as retinoic acid, vitamin A, LG100268, or LGD1069, wnt inhibitor such as dickkopf homolog 1 (DKK1).

In some embodiments, the cardiac neural crest cells can have a concentration of stem cell factor-receptors of about 50 receptors/micrometer$^2$ to about 800 receptors/micrometer$^2$. In other embodiments, the cardiac neural crest cells can have a concentration of stem cell factor-receptors of about 200 receptors/micrometer$^2$ to about 600 receptors/micrometer$^2$.

Presently disclosed is also a method of producing cardiac neural crest cells. The method may include culturing a plurality of stem cells with noggin and leukemia inhibitory factor, culturing the plurality of stem cells with noggin, thereby forming three-dimensional aggregates of the plurality of stem cells, and culturing the plurality of stem cells in cardiac neural crest differentiation medium to form cardiac neural crest cells.

In some embodiments the cardiac neural crest cells express stem cell factor-receptor, and are cKit positive. In some embodiments, the plurality of stem cells are induced pluripotent stem cells or embryonic stem cells. In some embodiments, the noggin in the step of culturing a plurality of stem cells with noggin and leukemia inhibitory factor can be at a concentration of 150 ng/ml and the leukemia inhibitory factor is at a concentration of 2000 units/ml. In some embodiments, the cardiac neural crest cells can have a concentration of stem cell factor-receptors of about 50 receptors/micrometer$^2$ to about 800 receptors/micrometer$^2$, or about 200 receptors/micrometer$^2$ to about 600 receptors/micrometer$^2$. In other embodiments, the method can also include contacting tamoxifen to the stem cells.

Additionally disclosed is a pharmaceutical composition comprising cardiac neural crest cells and a pharmaceutically acceptable carrier or excipient. In some embodiments, the cardiac neural crest cells are cKit positive. In some embodiments, the cardiac neural crest cells can have a concentration of stem cell factor-receptors of about 50 receptors/micrometer$^2$ to about 800 receptors/micrometer$^2$ or about 200 receptors/micrometer$^2$ to about 600 receptors/micrometer$^2$.

DETAILED DESCRIPTION

Figure 1:
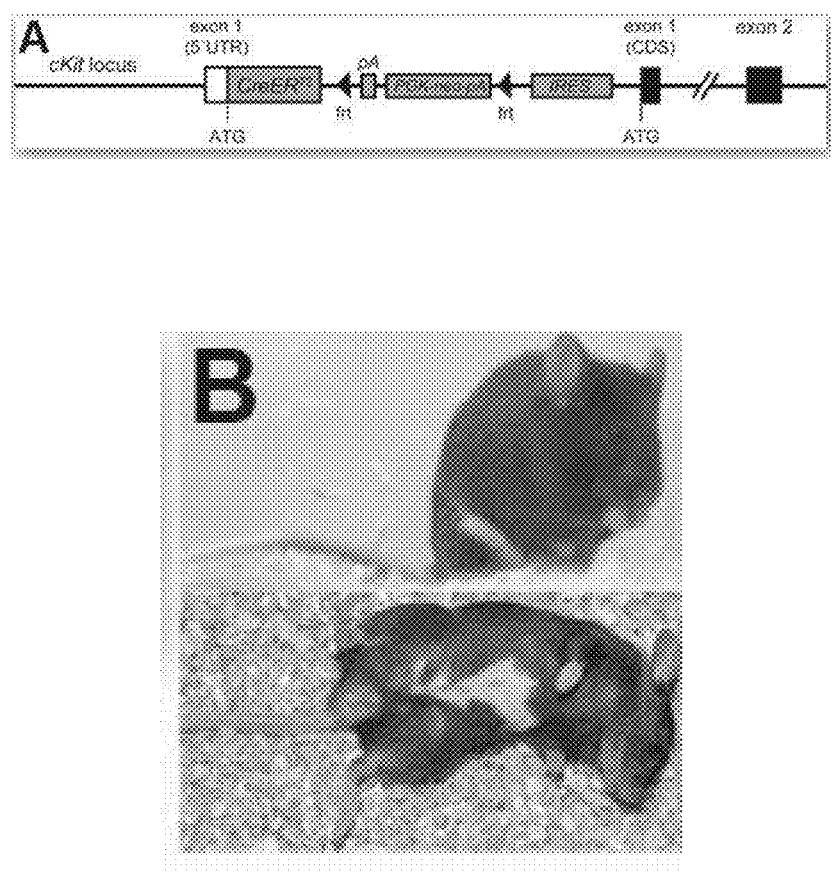
FIG. 1 shows a schematic illustration of the CreER$^{T2}$ knock-in allele; UTR: untranslated region, CDS: coding sequence (A) and a photograph illustrating the phenotype of cKit$^{CreERT2/+}$ mice (B).

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise.

As used herein, the term "about" means plus or minus 10% of the numerical value of the number with which it is being used. Therefore, about 50% means in the range of 45%-55%.

"Optional" or "optionally" may be taken to mean that the subsequently described structure, event or circumstance may or may not occur, and that the description includes instances where the event occurs and instances where it does not.

As used herein, the term "cell medium" or "cell media" is used to describe a cellular growth medium in which mononuclear cells and/or neural cells are grown. Cellular media are well known in the art and comprise at least a minimum of essential medium plus optional agents such as growth factors, glucose, non-essential amino acids, insulin, transferrin and other agents well known in the art.

Standard techniques for growing cells, separating cells, and where relevant, cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

The term "subject" or, in some instances, "patient" is used throughout the specification within context to describe an animal. The terms "subject" and "patient" can be used interchangeably. The animal can be human or non-human. In some embodiments, the subject is what is commonly referred to as a veterinary animal. Examples of a veterinary animal include, but are not limited to, dogs, cats, pigs, horses, birds, and the like. The subject can also be a non-human primate, such as, but not limited to, a monkey or chimpanzee.

Embodiments of the invention described herein are directed to neural crest cells that are predisposed to differentiating into cardiac cells, "cardiac neural crest cells," and various compositions including cardiac neural crest cells, therapeutic methods for using cardiac neural crest cells. Further embodiments are directed to methods for extracting cardiac neural crest cells from donor tissue, methods of producing cardiac neural crest cells, and preparing the cardiac neural crest cells for incorporation into a therapeutic composition and delivery to a patient. The cardiac neural crest cells of various embodiments are predisposed to differentiate into cardiac cells and are capable of differentiating into cells having a variety of phenotypes including, for example, various types of cardiomyocytes, epicardial and conduction system cells, and melanocytes. Thus, in particular embodiments, the cardiac neural crest cells and compositions including cardiac neural crest cells may be useful for cell-based therapeutic regeneration of cardiac tissues.

Specifically, cardiac neural crest cells are a distinct, transiently-formed, migratory, embryonic cell lineage which contributes to the development of the mammalian heart. Prior to the embodiments described herein, the role and existence of cardiac neural crest in the developing heart and postnatal heart was uncertain. In addition, prior to the present embodiments there existed a lack of a reliable methods to re-derive them from adult mammals, as well as the lack of a cell-surface marker that can subsequently serve for immunologically identifying and purifying them from heterogeneous cell mixtures, have compromised their potential for cell-based therapies. The present embodiments have unexpectedly resolved these uncertainties and provide reliable methods for obtaining such cells from a sample. Other surprising methods and compositions are provided herein.

Certain embodiments are directed to pharmaceutical compositions including cardiac neural crest cells. In such pharmaceutical compositions, the cardiac neural crest cells may be any of the cardiac neural crest cells described above, and such cardiac neural crest cells can be derived from any source. In some embodiments, the cardiac neural crest cells may exhibit a cell surface concentration of cKit within the ranges defined above, and in particular embodiments, the cardiac neural crest cells may include additional genetic material for exogenous protein expression. The pharmaceutical compositions may include cardiac neural crest cells alone, or in certain embodiments, the pharmaceutical composition may include additional non-neural crest cells that allow the cardiac neural crest cells to remain viable prior to administration or that induce the cardiac neural crest cells to exhibit or maintain a particular phenotype. In such embodiments, the cardiac neural crest cells may make up the majority of the live cells in the pharmaceutical composition. In some embodiments, the pharmaceutical composition comprises mesenchymal and/or cardiac stem cells. In some embodiments, the ratio of mesenchymal stem cells to cardiac stem cells is about 30:1. In some embodiments, the ratio is about 10:1 to about 50:1. In some embodiments, the ratio of mesenchymal stem cells to cardiac stem cells is about 20:1 to about 50:1. In some embodiments, the ratio of mesenchymal stem cells to cardiac stem cells is about 30:1 to about 50:1. In some embodiments, the ratio of mesenchymal stem cells to cardiac stem cells is about 40:1 to 50:1. For example, in such embodiments, the pharmaceutical compositions may include at least about 50% by weight, about 60% by weight, about 70% by weight, about 80% by weight, about 90% by weight cardiac neural crest cells, or any range between any of these values (including endpoints). In other embodiments, the pharmaceutical composition may include about 50% by weight to about 100% by weight, about 60% by weight to about 95% by weight, about 70% by weight to about 90% by weight cardiac neural crest cells, or any range between any of these values (including endpoints). In some embodiments, the pharmaceutical compositions may include a pharmaceutically acceptable carrier or excipient as described below. In such embodiments, the total amount of the cardiac neural crest cells in the pharmaceutical composition may be from about $1\times10^5$ cells, about $1\times10^6$ cells, about $1\times10^7$ cells, about $1\times10^8$ cells, about $1\times10^9$ cells, about $1\times10^{10}$ cells, or any range between any of these values (including endpoints). In such embodiments, the total amount of the cardiac neural crest cells in the pharmaceutical composition may be from about $1\times10^3$ to about $1\times10^{10}$ cells, or in other embodiments, about $1\times10^4$ to about $1\times10^9$, about $1\times10^5$ to about $1\times10^8$, or any range between any of these values (including endpoints).

In some embodiments, the pharmaceutical composition may include one or more differentiation agents that aid in the differentiation of the cardiac neural crest cells or other cells associated with the injury. For example, in some embodiments, the pharmaceutical composition may include BMP antagonist, noggin, chordin, Tsg, soluble receptors such as BMPR1A and BMPR1B, small molecule BMP antagonist such as dorsomorphin, retinoic acid receptor agonist such as retinoic acid, vitamin A, LG100268, or LGD1069, wnt inhibitor such as dickkopf homolog 1 (DKK1), and the like and combinations thereof. The differentiation agents may by combined in the pharmaceutical before administration or, in other embodiments, the differentiation agent may be applied to the injury after administration of a pharmaceutical composition including cardiac neural crest cells. In still other embodiments, the differentiation agent may be encapsulated in, for example, a liposome that allows for release of the differentiation agent after administration of the pharmaceutical composition.

In some embodiments, the pharmaceutical composition may include one or more active agents intended for administration to the patient. For example, in some embodiments, the pharmaceutical composition may further include antifungals, antibacterials, antivirals, steroids, anti-inflammatory drugs, nonsteroidal anti-inflammatory drugs, chemotherapeutics, anti-apoptotic agents, antioxidants, antiemetics, and the like and combinations thereof. More particular examples of active agents that may be added to pharmaceutical compositions of embodiments, include, but are not limited to, extracellular matrix components, such as one or more types of collagen, growth factors, platelet-rich plasma, anti-apoptotic agents such as erythropoietin (EPO), EPO mimetibody, thrombopoietin, insulin-like growth factor (IGF)-I, IGF-II, hepatocyte growth factor, caspase inhibitors, anti-inflammatory compounds such as p38 MAP kinase inhibitors, TGF-beta inhibitors, statins, IL-6 and IL-1 inhibitors, PEMIROLAST, TRANILAST, REMICADE, SIROLIMUS, non-steroidal anti-inflammatory drugs (NSAIDS) such as TEPDXALIN, TOLMETIN, and SUPROFEN, immunosuppressive or immunomodulatory agents, such as calcineurin inhibitors, mTOR inhibitors, antiproliferatives, corticosteroids, and various antibodies, antioxidants such as probucol, vitamins C and E, conenzyme Q-10, glutathione, L-cysteine and N-acetylcysteine, local anesthetics, and the like and combinations thereof.

Pharmaceutical compositions of the invention including neural crest cells or cardiac neural crest cells, one or more differentiation agent, and/or one or more active agent can be formulated with a pharmaceutically acceptable carrier or medium. Such compositions include solutions of the cells, cell preparations, or cellular compositions in association with one or more pharmaceutically acceptable vehicles or diluents, and contained in buffered solutions with a suitable pH and iso-osmotic with the physiological fluids. Suitable pharmaceutically acceptable carriers include, for example, water, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized before combining with the NCC and additional components. In certain embodiments, the pharmaceutical agents may include one or more auxiliary agents such as, for example, lubricants, preservatives, stabilizers, wetting agents, emulsifiers, salts for influencing osmotic pressure, buffers, and coloring. Pharmaceutical carriers suitable for use in the present invention are known in the art and are described, for example, in suitable vehicles in Remington's Pharmaceutical Sciences (Remington's Pharmaceutical Sciences, Mack Publishing Company, Easton, Pa., USA 1985).

Pharmaceutical compositions including live cells are typically formulated as liquids, semisolids (e.g., gels), or solids (e.g., matrices, scaffolds and the like, as appropriate for neural tissue engineering). Liquid compositions are formulated for administration by any acceptable route known in the art to achieve delivery of live cells to the target tissue. For example, delivery can be achieved by injection or infusion, either systemically, locally, or by targeted injection or infusion at the site of injury.

Pharmaceutical compositions including live cells in a semi-solid or solid carrier are typically formulated for surgical implantation at the site of injury. Notably, liquid compositions can also be administered by surgical procedures. In particular embodiments, semi-solid or solid pharmaceutical compositions may include semi-permeable gels, lattices, cellular scaffolds, and the like, which may be biodegradable or non-biodegradable. For example, in some embodiments, cardiac neural crest cells may be sequestered from their surroundings, but capable of secreting and delivering biological molecules to surrounding cells by producing an autonomous implant comprising living cardiac neural crest cells surrounded by a non-degradable, selectively permeable barrier that physically separates the transplanted cells from host tissue. Such implants are sometimes referred to as "immunoprotective," as they have the capacity to prevent immune cells and macromolecules from killing the transplanted cells in the absence of pharmacologically induced immunosuppression.

In other embodiments, the pharmaceutical compositions may include degradable gels and networks. Degradable materials may be particularly suitable for sustained release formulations including biocompatible polymers, such as poly(lactic acid), poly (lactic-co-glycolic acid), methylcellulose, hyaluronic acid, collagen, and the like. The structure, selection and use of degradable polymers in drug delivery vehicles are known in the art. In other embodiments, the cardiac neural crest cells may be provided on or in a biodegradable, bioresorbable, or bioabsorbable, scaffold or matrix. These typically three-dimensional biomaterials contain the living cells attached to the scaffold, dispersed within the scaffold, or incorporated in an extracellular matrix entrapped in the scaffold. Once implanted into the target region of the body, these implants become integrated with the host tissue, and the transplanted cells gradually become established. Examples of scaffold or matrix (sometimes referred to collectively as "framework") material include nonwoven mats, porous foams, self-assembling peptides, and the like and combinations thereof. Nonwoven mats may, for example, be formed using fibers of a synthetic absorbable copolymer of glycolic and lactic acids (PGA/PLA). Foams composed of, for example, poly(epsilon-caprolactone)/poly(glycolic acid) (PCL/PGA) copolymer, can be formed by processes such as freeze-drying, or lyophilized. In further embodiments, the pharmaceutical composition may include hydrogels such as self-assembling peptides (e.g., RAD16), and in still other embodiments, the pharmaceutical composition may be in situ-formed degradable networks that are formulated as fluids suitable for injection that are induced to form a degradable hydrogel networks in situ or in vivo by, for example, a change in temperature, pH, exposure to light.

In some embodiments, the framework may be a felt that can be composed of a multifilament yarn made from a bioabsorbable material such as PGA, PLA, PCL copolymers or blends, hyaluronic acid, and the like or combinations thereof. The yarns can be made into a felt using standard textile processing techniques consisting of crimping, cutting, carding and needling. In other embodiments, the framework can be a bioadsorbable composite foam scaffold. The framework of such embodiments may be molded into a useful shape to create various pre-formed surgical or implantable devices.

The cardiac neural crest cells may be introduced on to the framework, or device at any time. For example, in some embodiments, cardiac neural crest cells can be seeded onto the framework prior to implantation, and in other embodiments, the cardiac neural crest cells may be cultured on framework. In some embodiments, framework may be treated prior to inoculation of cells in order to enhance cell attachment. For example, prior to inoculation, nylon matrices can be treated with 0.1 molar acetic acid and incubated in polylysine, PBS, and/or collagen to coat the nylon. Polystyrene can be similarly treated using sulfuric acid. The external surfaces of a framework may also be modified to improve the attachment or growth of cells and differentiation of tissue by, for example, plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, and plant gums, among others.

In certain embodiments, the pharmaceutical composition may include cardiac neural crest cells and non-cardiac neural crest cells. For example, in some embodiments, cardiac neural crest cells can be combined or formulated with mesenchymal cells, endothelial cells, smooth muscle cells, fibroblast cells, and the like and combinations thereof. In some embodiments, the cardiac neural crest cells and/or the non-cardiac neural crest cells in the pharmaceutical composition may be obtained or derived from the subject that is to be treated either through separate extractions or by causing the cardiac neural crest cells to take on a more differentiated form such as endothelial cells, smooth muscle cells, fibroblast cells, and the like or combinations thereof, and in particular embodiments, pharmaceutical compositions including non-cardiac neural crest cells may be in the form of a tissue patch. In particular embodiments, the non-cardiac neural crest cells may be present as a result of the natural differentiation of the cardiac neural crest cells.

Further embodiments are directed to a method of producing cardiac neural crest cells. The cardiac neural crest cells of various embodiments can be isolated from a variety of sources including, but not limited to, fetal hearts, and the source species can vary based on the species into which the cardiac neural crest cells are to be implanted. For example, cardiac neural crest cells for use in humans can be isolated from human fetal hearts, and cardiac neural crest cells for use in dogs may be isolated from dogs. Similarly, cardiac neural crest cells for use in horses, pigs, or other mammals can be isolated from fetal hearts derived from that animal.

In other embodiments, cardiac neural crest cells can be obtained from stem cells that have been induced to act as neural crest cells. The stem cells can be embryonic stem cells or induced pluripotent stem cells. Embryonic stem cells are typically derived from embryonic tissue. Induced pluripotent cells can be derived from a number of sources including, for example, skin, blood, umbilical cord blood, bone marrow, and skin, and these tissues can be obtained from adults. The multipotent or pluripotent cells can be harvested from these tissues, and neural crest cell-like activity can be induced through various means. For example, in some embodiments, embryonic stem cells or adult multipotent or pluripotent cells can be cultured with MS5 stromal cells to produce stem cells that exhibit a neural crest cell-like phenotype. In other embodiments, embryonic stem cells or adult multipotent or pluripotent cells can be cultured with, for example, fibroblast growth factor 2 (FGF2), bone morphogenic protein 2 (BMP2), BMPR1A, BMPR1B, noggin, chordin, Tsg, small molecule BMP antagonist such as dorsomorphin, retinoic acid receptor agonist such as retinoic acid, vitamin A, LG100268, or LGD1069, wnt inhibitor such as dickkopf homolog 1 (DKK1), and the like and combinations thereof to produce stem cells that exhibit a neural crest cell-like phenotype. In particular embodiments, skin-derived precursor cells or epidermal neural crest cells can be isolated from adult skin. In certain embodiments, such cells may be isolated from the skin of the patient into which the cardiac neural crest cells will be transplanted, and in some embodiments, the skin-derived precursor cells or epidermal neural crest cells may be cultured to induce a particular phenotype by, for example, culturing in the presence of other cells or culturing the presence of one or more growth factors, or to increase the number of cardiac neural crest cells. In other embodiments, somatic cells can be reprogrammed into induced pluripotent stem cells by any means known in the art.

Cardiac neural crest differentiation medium can be used during the culturing process of stem cells. Cardiac neural crest differentiation medium can include growth medium, fetal bovine serum, antibiotics, and antimycotics. In some embodiments, the growth medium can be selected from Iscove's Modified Dulbecco's Medium (IMDM), Dulbecco's Modified Eagle Medium (DMEM), Minimum Essential Medium (MEM), Essential 6™ Medium, Essential 8™ Medium, Roswell Park Memorial Institute 1640 Medium, F10 Nutrient Mixture, Ham's F12 Nutrient Mixture, Media 199, or any combination thereof. In some embodiments, the antibiotics can be selected from actinomycin D, ampicillin, carbenicillin, cefotaxime, fosmidomycin, gentamicin, kanamycin, neomycin, penicillin streptomycin, polymyxin B, streptomycin, or any combination thereof. In some embodiments the antimycotic can be selected from amphotericin B, nystatin, natamycin, echinocandin, flucytosine, or any combination thereof. In particular embodiments, the cardiac neural crest differentiation medium can include IMDM, fetal bovine serum, and penicillin streptomycin.

In some embodiments the cardiac differentiation medium can include fetal bovine serum at a volume percent of about 1%, about 5%, about 10%, about 15%, about 20%, about 25%, about 30%, about 35%, about 40%, about 45%, about 50%, or a range between any of these values (including endpoints). In some embodiments, the cardiac neural crest differentiation medium can include a volume percent of 20% fetal bovine serum.

In some embodiments, the cardiac differentiation medium can include antibiotics at a volume percent of about 0.25%, about 0.5%, about 1%, about 2%, about 3%, about 4%, about 5%, about 10%, about 15%, about 20%, or a range between any of these values (including endpoints). In some embodiments, the cardiac neural crest differentiation medium can include a volume percent of 1% antibiotics.

In some embodiments, the cardiac differentiation medium can include antimycotics at a volume percent of about 0.25%, about 0.5%, about 1%, about 2%, about 3%, about 4%, about 5%, about 10%, about 15%, about 20%, or a range between any of these values (including endpoints).

A plurality of stem cells can be cultured with noggin and leukemia inhibitory factor (LIF). The stem cells can be embryonic stem cells or induced pluripotent stem cells. In some embodiments, the stem cells are induced pluripotent stem cells. The stem cells can be cultured in gelatinized dishes or non-adherent dishes. In some embodiments, the stem cells can be cultured in gelatinized dishes. The stem cells can be cultured for about 1 day, about 2 days, about 3 days, about 4 days, about 5 days, about 6 days, about 7 days, about 8 days, about 9 days, about 10 days, or a range between any of these values (including endpoints). In some embodiments, the stem cells are cultured in gelatinized dishes for 3 days. In some embodiments, the stem cells can be detached from the dish and cultured for 1 day in non-adherent dishes with cardiac neural crest differentiation medium and noggin. The stem cells can be detached by rinsing the cells with cardiac neural crest differentiation medium to remove any serum in the dish, and dissociating the stem cells from the dish by using a trypsin solution. The trypsin solution can contain a volume percent of about 0.5% trypsin, about 1% trypsin, about 2% trypsin, about 3% trypsin, about 4% trypsin, about 5% trypsin, about 10% trypsin, about 20% trypsin, about 25% trypsin, about 30% trypsin, or a range between any of these values (including endpoints). In other embodiments, the stem cells can be dissociated from the dish by scraping the cells off of the dish.

Noggin can be added to the stem cells at a concentration of about 25 ng/ml, about 35 ng/ml, about 40 ng/ml, about 45 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, or a range between any of these values (including endpoints).

LIF can be added to the stem cells at a concentration of about 100 units/ml, about 125 units/ml, about 150 units/ml, about 200 units/ml, about 300 units/ml, about 500 units/ml, about 750 units/ml, about 1000 units/ml, about 1,100 units/ml, about 1,200 units/ml, about 1,400 units/ml, about 1,600 units/ml, about 1,800 units/ml, about 2,000 units/ml, about 2,200 units/ml, about 2,400 units/ml, about 2,600 units/ml, about 2,800 units/ml, about 3,000 units/ml, or a range between any of these values (including endpoints). In some embodiments, the noggin can be at a concentration of 150 ng/ml and the leukemia inhibitory factor is at a concentration of 2000 units/ml when culturing a plurality of stem cells with noggin and leukemia inhibitory factor.

The plurality of stem cells can be further cultured with noggin. The noggin can be added to the stem cells at any concentration mentioned previously. In some embodiments, the plurality of stem cells can thereby form three-dimensional aggregates of the plurality of stem cells. The three-dimensional aggregates of the stem cells are also called embryoid bodies.

The plurality of stem cells can be furthered cultured with cardiac neural crest differentiation medium to form cardiac neural crest cells. In some embodiments, the cardiac neural crest cells are beating neural crest cells. The cardiac neural crest cells can also be further isolated and/or purified. In some embodiments, the medium does not contain noggin. In some embodiments, the plurality of stem cells are embryoid bodies. In some embodiments, the embryoid bodies are cultured in non-adherent dishes with cardiac neural crest differentiation medium. The embryoid bodies are cultured for about 1 day, about 2 days, about 3 days, about 4 days, about 5 days, about 6 days, about 7 days, about 8 days, about 9 days, about 10 days, or a range between any of these values (including endpoints). In some embodiments, the embryoid bodies are cultured in non-adherent dishes with cardiac neural crest differentiation medium for 4 days.

The plurality of stem cells can be contacted with tamoxifen. The tamoxifen can be added after the plurality of stem cells are further cultured with cardiac neural crest differentiation medium. In some embodiments, the tamoxifen can be 4-OH tamoxifen. The tamoxifen can be added to the embryoid bodies of the plurality of stem cells about 1 day after the further culturing step with cardiac neural crest differentiation medium, about 2 days after, about 3 days after, about 4 days after, about 5 days after, about 6 days after, about 7 days after, about 8 days after, about 9 days after, about 10 days after, or any range between any of these values (including endpoints). The tamoxifen can be removed from the embryoid bodies of the plurality of stem cells after about 1 day of exposure, about 2 days of exposure, about 3 days of exposure, about 4 days of exposure, about 5 days of exposure about 6 days of exposure, about 7 days of exposure, about 8 days of exposure, about 9 days of exposure, about 10 days of exposure, or any range between any of these values (including endpoints). In some embodiments, the embryoid bodies of the plurality of stem cells can be pulsed with tamoxifen. In other embodiments, the embryoid bodies of the plurality of stem cells have 4-OH tamoxifen added 4 days after further culturing the plurality of stem cells with cardiac differentiation medium, and 4-OH tamoxifen removed after 3 days of exposure to 4-OH tamoxifen.

In further embodiments, the embryoid bodies are transferred to gelatinized plates on day 4. In further embodiments, the embryoid bodies are continued to be cultured in the gelatinized plates until the embryoid bodies form beating colonies of cardiac neural crest cells. The embryoid bodies can form beating colonies of cardiac neural crest cells after about 1 day, about 2 days, about 4 days, about 5 days, about 6 days, about 8 days, about 10 days, about 12 days, about 14 days, about 15 days, about 16 days, about 18 days, about 20 days, about 25 days, or a range between any of these values (including endpoints).

In some embodiments, cardiac neural crest cells express stem cell factor-receptor (cKit), a receptor tyrosine kinase that is displayed on an outer surface of the cell membrane. In some embodiments, the cardiac neural crest cells are cKit positive. As the cardiac neural crest cells differentiate, the concentration of cell surface concentration of cKit diminishes, and fully differentiated cells, typically, have a cell surface concentration of cKit of about 0 receptors/micrometer$^2$. Accordingly, the cell surface concentration of cKit can vary among embodiments and can be any concentration sufficient to allow the cardiac neural crest cells to differentiate. For example, in some embodiments, the cardiac neural crest cells may have a cell surface concentration of cKit that is at least greater than about 50 receptors/micrometer$^2$, and in other embodiments, the cell surface concentration of cKit for the cardiac neural crest cells may be from about 50 receptors/micrometer$^2$ to about 800 receptors/micrometer$^2$, about 100 receptors/micrometer$^2$ to about 700 receptors/micrometer$^2$, about 200 receptors/micrometer$^2$ to about 600 receptors/micrometer$^2$, or any individual cell surface concentration or range of cell surface concentrations encompassed by these ranges.

In some embodiments, the cardiac neural crest cells may be substantially unmodified meaning that the cardiac neural crest cells are not intentionally genetically modified after being extracted from the parent tissue (e.g., fetal heart tissue). In other embodiments, the cardiac neural crest cells may be genetically manipulated to produce a desired phenotype. Such genetic modification may be the result of introducing genetic material into the cell after extraction or genetic modification of the parent tissue. For example, in some embodiments, a population of cardiac neural crest cells extracted from parent tissue may be transformed with genetic material for expression of exogenous proteins such as, for example, markers, hormones, signaling peptides or proteins, and the like and combinations thereof. In particular embodiments, genetic material may be introduced into gametes, fertilized eggs (i.e., zygotes), or early stage embryos that allow for expression of such exogenous proteins.

Further embodiments are directed to methods for making neural crest cells and methods for making pharmaceutical compositions including the neural crest cells. In some embodiments, the neural crest cells may be fetal neural crest cells that are extracted from a human embryo. Methods for extracting fetal neural crest cells can vary among embodiments and can include the steps of digesting fetal heart tissue with a collagenase to create explanted fetal heart cells, introducing the fetal heart cells into a growth medium, separating fetal heart cells expressing cKit from other fetal heart cells not expressing cKit, and expanding the fetal heart cells expressing cKit. The steps of digesting fetal heart tissue can be carried out by any method using any enzyme capable of breaking down extracellular matrix components and freeing individual cells or groups of cells from tissues, including, for example, collagenases, trypsins, elastases, hyaluronases, papains, chymotrypsins, proteases, and the like and various combinations thereof. In certain embodiments, digesting can be carried out using a collagenase, such as, Collagenase-Type II. Similarly, the growth medium can be any growth medium known in the art that is capable of sustaining human cells. In some embodiments, the growth medium may be a solid growth medium onto which the fetal heart cells or neural crest cells are seeded, and in other embodiments, the growth medium may be a liquid growth medium. In embodiments in which liquid growth media is used, the liquid media may be agitated, aerated, or the like and combinations thereof, to ensure that the cells in the growth media remain separated. In certain embodiments, the growth medium may be supplemented with growth factors, antibiotics, non-essential amino acids, and the like and combinations thereof. In particular embodiments, the medium may include growth factors such as, but not limited to, one or more cytokines, leukemia inhibitory factor (LIF), fibroblast growth factors (FGF), stem cell factor (SCF), and the like and combinations thereof. The antibiotics included in growth media may be selected to reduce the likelihood of bacterial growth in the media. Any known antibiotic can be used including, but not limited to, Actinomycin D, Ampicillin, Carbenicillin, Cefotaxime, Fosmidomycin, Gentamicin, Kanamycin, Neomycin, Penicillin Streptomycin (Pen Strep), Polymyxin B, Streptomycin Sulfate, and the like and combinations thereof. Separating can be carried out by any means, and in certain embodiments, separating can be carried out by cell sorting using anti-cKit antibodies that have been conjugated to a fluorescent probe, such as, for example, allophycocyanin (APC). Expanding can be carried out by, for example, introducing the separated neural crest cells into a growth medium such as those described above for sufficient time to allow the cells to reproduce.

The methods of other embodiments can include the steps of extracting multipotent or pluripotent cells from a patient, inducing the multipotent or pluripotent cells to exhibit a cardiac neural crest cell-like phenotype, and contacting an injury with the multipotent or pluripotent cells. The step of extracting multipotent or pluripotent cells can be carried out by any means. For example, in some embodiments, multipotent or pluripotent cells can be extracted from skin cells by obtaining a skin graft from a patient. In other embodiments, stem cells can be derived from tissue containing regenerative cells which can be extracted from, for example, bone marrow, adipose tissue, blood, and the like. In certain embodiments, the multipotent or pluripotent cells can be from the patient, i.e., autologous stem cells, and in other embodiments, the multipotent or pluripotent cells can be obtained from a donor. Such methods can further incorporate steps described above such as digesting a tissue containing multipotent or pluripotent cells to create explanted multipotent or pluripotent cells, introducing the multipotent or pluripotent into a growth medium, separating multipotent or pluripotent cells expressing cKit from other multipotent or pluripotent not expressing cKit, and expanding the multipotent or pluripotent cells expressing cKit. In particular embodiments, such methods may further include treating the explanted multipotent or pluripotent cells with one or more proteins, cytokines, or other growth factors that allow the multipotent or pluripotent cells to take on a neural crest cell-like phenotype. For example, in some embodiments, multipotent or pluripotent cells can be expanded in the presence of flt 3 ligand, interleukin 6, interleukin 7, which have been shown to induce cKit expression in pluripotent cells, and like and combinations thereof, and such treatment may produce cells having a neural crest like phenotype.

In some embodiments, growth media may include feeder cells or other cells that aid in the growth of the neural crest cells. For example, feeder cells can produce certain nutrients necessary for neural crest cell growth that cannot be provided from other sources. Such feeder cells are well known and can include, for example, mesenchymal stem cells, embryonic stem cells, embryonic fibroblasts, and modified or immortalized versions of these cells. In some embodiments, the feeder cells may be derived from a non-human species, such as mouse or swine. In other embodiments, the feeder cells may be derived from human cells, and in certain embodiments, the feeder cells may be derived from the patient (i.e., autologous feeder cells). In particular embodiments, additional cells may be provided in the growth media that allow the fetal heart cells to take on a more tissue-like appearance. For example, in some embodiments, the growth media for expansion may include multi-potent or pluripotent mesenchymal stem cells, fibrocytes, or other human tissue cells, such as cardiac cells, that can allow the neural crest cells to be incorporated into a tissue-like mass.

In still other embodiments, the neural crest cells may be seeded onto a scaffold and induced to grow to produce structured tissue patch or artificial organ structure. For example, in some embodiments, the neural crest cells may be seeded onto a scaffold to produce an artificial artery or vein, and in other embodiments, the neural crest cells can be incorporated into a flexible tissue patch that can be placed on injured cardiac tissue.

In certain embodiments, the neural crest cells may be administered in a pharmaceutical composition, as described above, including at least an effective amount of the neural crest cells, and in some embodiments, the pharmaceutical composition may include one or more active agents such as those described above. In such embodiments, the methods may include combining neural crest cells with one or more pharmaceutically acceptable carrier or excipient. In some embodiments, methods for preparing a pharmaceutical composition may include isolating neural crest cells from other cells and components in an expansion growth medium using, for example, cell sorting, before combining with a pharmaceutically acceptable carriers or excipients. Some methods may include the step of incorporating one or more active agents into the pharmaceutical composition including neural crest cells. In other embodiments, methods may include the step of administering an active agent separately from the pharmaceutical composition including neural crest cells. Administrating the active agent can occur before or after administering the pharmaceutical composition including neural crest cells, and the active agent can be administered locally or systemically.

Further embodiments are directed to methods of treatment using cardiac neural crest cells, pharmaceutical compositions including cardiac neural crest cells, and medical devices including cardiac neural crest cells. Such embodiments may include the step of contacting an injury with a composition or device including cardiac neural crest cells. Such methods are not limited by the type of injury, and in particular embodiments, the injury may be a cardiac injury caused by, for example, myocardial infarction, heart failure, cardiomyopathy, congenital heart disease, nutritional diseases, ischemic or non-ischemic cardiomyopathy, hypertensive cardiomyopathy, valvular cardiomyopathy, inflammatory cardiomyopathy, cardiomyopathy secondary to a systemic metabolic disease, alcoholic cardiomyopathy, diabetic cardiomyopathy, restrictive cardiomyopathy, and the like and combinations thereof. In some embodiments, the cardiac neural crest cells express cKit, and are cKit positive. In some embodiments, the cardiac neural crest cells are cKit positive. In some embodiments, contacting may be effected by systemic delivery of a pharmaceutical composition including cardiac neural crest cells. In other embodiments, contacting may be effected by local delivery of cardiac neural crest cells or a pharmaceutical composition containing cardiac neural crest cells or directly contacting the site of injury with cardiac neural crest cells, a pharmaceutical composition including cardiac neural crest cells or medical device including cardiac neural crest cells. For example, in certain embodiments, cardiac neural crest cells may be implanted in as cells or pharmaceutical compositions by direct injection to the infarct area, injection with a catheter or implanted as a cardio-patch by a surgery.

The cardiac neural crest cells may, typically, be administered in a therapeutically effective amount. A therapeutically effective amount is any amount sufficient to provide treatment or prevention of the disease or injury being treated. The effective amount may vary among embodiments based, for example, on the severity of the condition, route of administration, dose frequency, age, body weight, physical condition, and the response of the individual patient. The attending physician can determine the effective amount based on these and other considerations and can determine how and when to terminate, interrupt, or adjust the effective amount by, for example, lowering the dosage due to toxicity or adverse effects or, conversely, increasing the effective amount if the clinical response is not adequate.

In some embodiments, the methods for treatment may include the step of administering one or more active agents in combination with the cardiac neural crest cells, pharmaceutical composition including cardiac neural crest cells, or medical device including cardiac neural crest cells, and in other embodiments, the step of administering one or more active agents may be carried out before contacting with cardiac neural crest cells, pharmaceutical composition including cardiac neural crest cells, or medical device including cardiac neural crest cells or after the step of contacting with cardiac neural crest cells, pharmaceutical composition including cardiac neural crest cells, or medical device including cardiac neural crest cells. The active agent may be any of the active agents described above, and in certain embodiments, the active agent may be formulated to prevent, treat, or delay a cardiac injury, disease, or disorder. The one or more active agents can be administered in an effective amount, and as discussed above, the physician can determine an effective amount of each active agent administered taking into account the considerations described above, e.g., severity of the condition treated, physical condition of the patient, etc., as well as other considerations specific to the individual active agents.

In some embodiments, administering may be carried out by implanting a scaffold containing neural crest cells or a tissue patch including neural crest cells into the patient. In some embodiments, such scaffolds may include biocompatible polymers or engineered tissues that provide a structure for the neural crest cells. The scaffold or tissue patch may be surgically implanted by, for example, removing diseased or injured tissue and implanting the scaffold or tissue patch including neural crest cells in place of the diseased or injured tissue. In other embodiments, surgically implanting may be carried out by removing diseased or injured tissue and contacting the wound produced by the surgical removal with neural crest cells, a combination of neural crest cells and other cells, or neural crest cells and other cells and one or more active agents.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples.

Example 1

Cells bearing the cKit receptor have been harnessed therapeutically to stimulate cardiac repair after injury. To identify the embryogenic source of these cells, fate mapping was carried out using a tamoxifen-inducible $cKit^{CreERT2/+}$ mouse line. Introducing tamoxifen sequentially during embryogenesis allowed for a direct identification of the origin of these cells and their contribution to cardiac formation.

$cKit^{CreERT2/+}$ mice were generated by homologous recombination as a knock-in of a $CreER^{T2}$ expression cassette into the ATG start codon at the endogenous cKit locus. Briefly, a targeting vector represented in FIG. 1, Panel A including a $CreER^{T2}$ cassette, an internal ribosome entry site, and a frt flanked neomycin resistance cassette was electroporated into 129S6 ES cells. Homologous recombination and single copy insertion was verified by Southern blot analysis and correctly targeted ES cells were injected into C57BL/6J blastocysts. Consistent with other heterozygous cKit mutants, $cKit^{CreERT2/+}$ are healthy and fertile, and characterized by the white spotting phenotype, FIG. 1, Panel B. The white spotting phenotype of $cKit^{CreERT2/+}$ mice, FIG. 1, Panel B, similar to other cKit mutants, is consistent with impaired melanogenesis and, therefore, suggests involvement of cKit in neural crest pathways.

Example 2

Genetic fate-mapping of cKit expressing cells was performed by crossing $cKit^{CreERT2/+}$ mice to two previously established Cre-reporter mouse lines; the dual fluorescent color-reporter DsRed/EGFP (IRG) or the beta-galactosidase-reporter $R26R^{lacZ}$. For the generation of embryos carrying a $cKit^{CreERT2}$/IRG; Isl1-nLacZ genotype, male $cKit^{CreERT2}$/IRG mice were crossed to female Isl1-nLacZ.

Cells actively expressing cKit 7.5 to 8.5 days post coitum (dpc) were identified by intraperitoneal injection of 100 µl of 20 mg/ml tamoxifen dissolved in peanut oil to pregnant mice carrying $cKit^{CreERT2}$/IRG embryos during this period and observing first or second heart-field myocardial progenitors. For assessing the role of cKit in first or second heart-field progenitors, mice carrying $cKit^{CreERT2}$/IRG or $cKit^{CreERT2}$/$R26R^{LacZ}$ embryos received a daily injection of tamoxifen for 2 consecutive days, during 7.5-8.5 dpc. Embryos were collected at 18.5 dpc, and EGFP expression was assessed via live tissue imaging, as well as confocal epifluorescence and immunofluorescence analyses in fixed samples.

Live tissue imaging illustrating rare EGFP epifluorescence showed successful recombination and was reflected in robust EGFP expression in circulating blood cells, testes and lungs (data not shown). Rarely, small, isolated EGFP$^{(+)}$ cells were detected in the heart (LV, left ventricle; LA, left atrium), which occasionally co-localized with the cardiac transcription factor Gata4, (data not shown), which shows confocal immunofluorescence of EGFP$^{(+)}$ cells co-expressing the cardiac lineage transcription factor Gata4 (arrowheads in insets). The arrow points to an EGFP$^{(+)}$ cell in epicardium, and the inset highlights 2 EGFP$^{(+)}$ cells that do not express Gata4 (data not shown).

Figure 2:
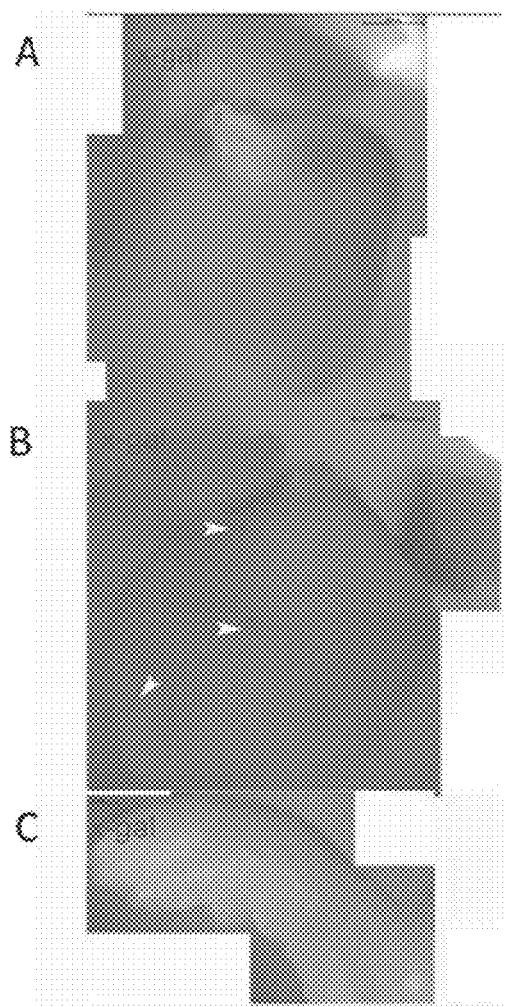
FIG. 2 shows photographs illustrating replication of 7.5-8.5 dpc lineage tracing in the cKit$^{CreERT2}$/R26R$^{lacZ}$ mouse (A-C).

None of the myocardial regions contained EGFP$^{(+)}$ myocardial progeny. Thus, genetic lineage tracing suggests that cKit does not mark first or second heart field myocardial progenitors. FIG. 2, Panels A-C shows no expression of X-gal in an 18.5 dpc heart of a WT littermate. In FIG. 2, Panel B, rare X-gal$^{(+)}$ cells (arrowheads) in the heart of a cKit$^{CreERT2}$/R26R$^{lacZ}$ littermate are shown. FIG. 2, Panel C shows that recombination in cKit$^{CreERT2}$/R26R$^{lacZ}$ during 7.5-8.5 dpc does not mark melanocytes, further supporting that the cKit$^{CreERT2}$ allele faithfully reflects endogenous cKit expression.

Example 3

Neural crest is known to contribute to cardiogenesis. To show this, mice carrying cKit$^{CreERT2}$/IRG or cKit$^{CreERT2}$/R26R$^{LacZ}$ embryos received a daily injection of tamoxifen for 3 consecutive days, either during 9.5-11.5 dpc or during 10.5-12.5 dpc, the embryonic stages during which cardiac NCCs supplement the mammalian cardiogenic program, to determine whether cKit delineates cells of cardiac NCC lineage. As expected, cKit$^{CreERT2/+}$-mediated recombination EGFP labeled embryonic melanoblasts, neural tube, dorsal root ganglia (DRGs), circulating blood cells, gastrointestinal cells, testes, and lungs were identified, (data not shown). However, in contrast to the genetic fate-map of 7.5-8.5 dpc cKit-expressing cells, robust EGFP epifluorescence was present within the cardiac outflow tract (OFT), epicardium, and myocardium in all of the live, beating cre/loxP recombined 18.5 dpc cKit$^{CreERT2}$/IRG embryonic hearts examined (data not shown). Thus, cKit$^{(+)}$ cardiac precursors appear to arise in large part from NCC cells which migrate at ~9.5 dpc to the developing heart where they contribute to cardiogenesis.

Because in other murine models specificity and efficiency of Cre-recombination vary between different Cre reporter alleles, leading to inconsistent results, the fate-mapping strategy using the cKit$^{CreERT2}$/R26R$^{lacZ}$ mice described above was used to verify the presence of the cKit$^{CreERT2/+}$ allele. Females with a vaginal plug were considered at 0.5 dpc. Embryos at different time points were harvested in ice-cold Hank's Balanced Salt solution (HBSS, Gibco). For 12.5 dpc and 18.5 dpc embryos carrying the cKit$^{CreERT2}$/IRG alleles, live-tissue imaging was performed immediately after dissection under a fluorescence microscope and EGFP and DsRed epifluorescence were photodocumented. Samples were then fixed for 1-1½h in 4% paraformaldehyde (PFA) at room temperature followed by overnight incubation in 30% sucrose at 4° C. The next day, samples were embedded in optimal cutting compound (OCT) and flash-frozen in liquid nitrogen before cryosectioning. X-gal staining was performed using a β-galactosidase staining kit in fixed intact mouse embryonic hearts or embryos carrying the cKit$^{CreERT2}$/R26R$^{LacZ}$ or Isl1-nLacZ alleles, as well as their respective littermates. Briefly, samples were incubated overnight in X-gal solution at 37° C. The next day, X-gal was washed away with PBS, samples were photodocumented under a light microscope and incubated overnight in 30% sucrose at 4° C. Fixed tissues were then embedded in OCT and processed for cryosectioning. In some instances of cKit$^{CreERT2}$/IRG; Isl1-nLacZ embryos, X-gal was performed after cryosectioning, following EGFP immunostaining. For cKit immunohistochemical analyses, 12.5-14.5 dpc wild-type mouse embryos were harvested and fixed overnight in 10% buffered formalin. The next day, these fixed embryos were embedded in paraffin and processed for immunohistochemistry.

Figure 3:
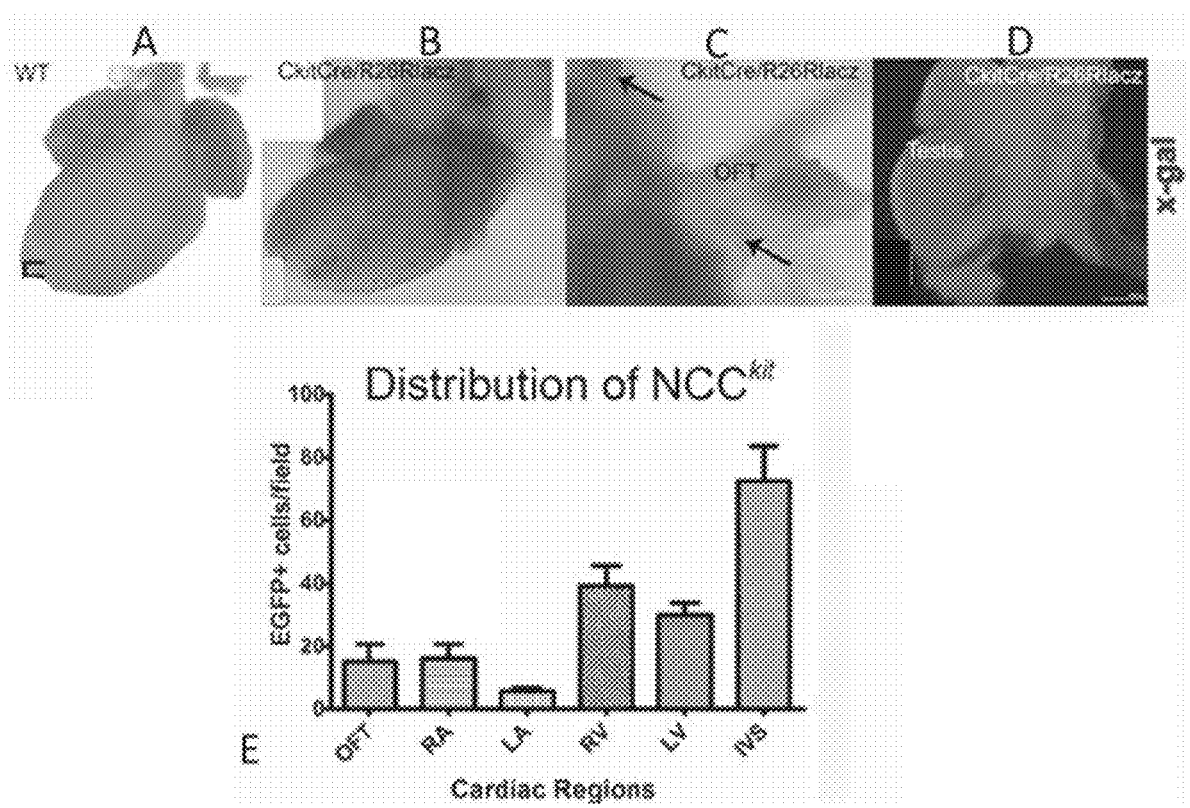
FIG. 3 are confocal images of an 18.5 dpc cKit$^{CreERT2}$/R26R$^{lacZ}$ heart exposed to tamoxifen during 9.5-11.5 dpc (A & B), X-gal$^{(+)}$ cells in OFT (C), X-gal$^{(+)}$ cells in the testis (D), and a graph illustrating the distribution of neural cardiac crest cells in the heart (E).
Figure 4:
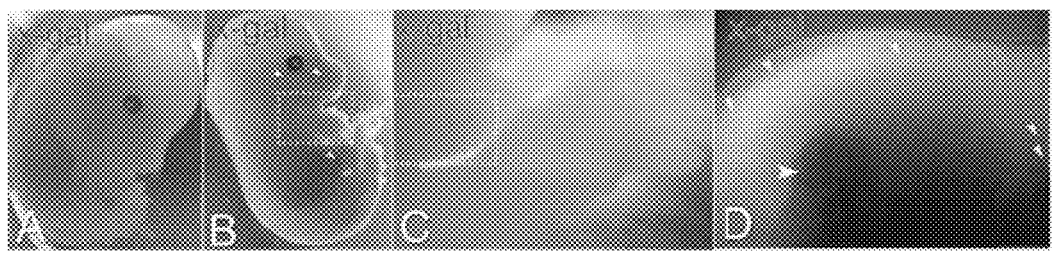
FIG. 4 shows X-gal in a 14.5 dpc WT embryo of a cKit$^{CreERT2}$/R26R$^{lacZ}$ litter, exposed to tamoxifen at 13.5 dpc exhibiting no X-gal staining (A); a littermate embryo carrying the cKit$^{CreERT2}$/R26R$^{lacZ}$ genotype exhibiting X-gal staining in urogenital area (arrow) and melanocytes (box and arrowheads in the head) (B); magnification of the boxed area in (B) illustrating X-gal$^{(+)}$ melanocytic cells (C); X-gal$^{(+)}$ cells in the liver and gut (large arrowhead) as well as in skin melanocytes and spine (small arrowheads) of the embryo in (B) and (D).

Histological assessment of the genetic fate-maps with X-gal revealed that recombination in cKit$^{CreERT2}$/R26R$^{lacZ}$ embryos produced mosaic patterns identical to cKit$^{CreERT2}$/IRG, FIG. 3, Panels A-D and FIG. 4, Panels A-D. FIG. 3, Panel E illustrates the distribution of neural cardiac crest cells in the heart. Thus, tamoxifen-induced Cre-recombination is specific for the cKit lineage and consistent between different lox-stop-lox silenced reporter-alleles.

As in other melanoblastic and neuroblastic NCC lineages, phenotypic analysis showed that NCC$^{kit}$ and their cardiac derivatives co-expressed the micropthalmia-associated transcription factor Mitf, (data not shown). For cryosections, 10 µm-thick samples were post-fixed for 10 min with 4% PFA. For paraffin-embedded tissues, 4-5 µm-thick tissue sections were deparaffinized and rehydrated. Antigen unmasking was performed by microwaving the slides for 2×10 min in citrate buffer Solution, pH=6 (Dako, Carpenteria, Calif.). Sections were then blocked for 1 h at RT with 10% normal donkey serum (Chemicon International Inc, Temecula, Calif.), followed by overnight incubation at 4° C. with the primary antibody. The following antibodies were used: cKit, EGFP, beta-galactosidase, Connexin-43, KDR, MITF, PECAM1, a-smooth muscle actin, Anti-Smooth Muscle Myosin Heavy Chain, cardiac troponin-I, Calponin, tropomyosin, Tyrosinase, cardiac myosin light chain-2v, Neurofilament-M, Nkx2.5, GATA-4, Isl-1, and Factor VIII-related antigen. Subsequently, the antibodies were visualized by incubating the sections for 1 h at 37° C. with FITC, Cy3 and Cy5-conjugated F(ab')$_2$ fragments of affinity-purified secondary antibodies. For MITF and SM1, tyramide signal amplification was employed. Slides were counterstained with DAPI, mounted with ProLong Antifade Gold reagent, and stored at 4° C. until further examination. Microscopic evaluations and image acquisitions were performed with a Zeiss LSM-710 Confocal Microscope. The Zeiss ZEN software was used. Notably, Mitf and cKit mutations cause similar melanocytic and myocardial defects. Thus, our findings imply that, as in melanogenesis, the relationship underlying cKit and Mitf pathways characterizes the NCC$^{kit}$ cardioblasts, as well.

Figure 6:
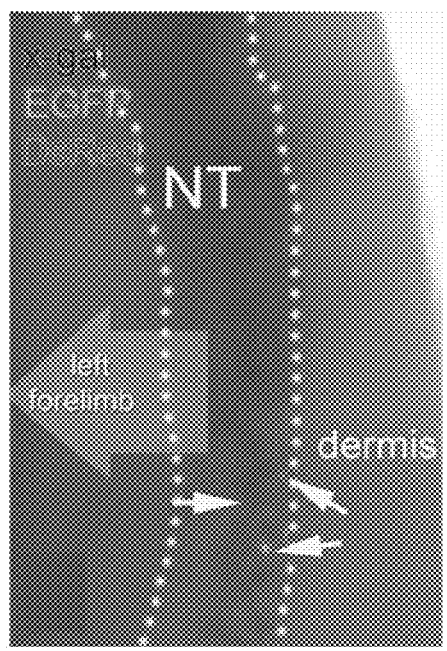
FIG. 6 shows whole mount imaging of a 12.5 dpc cKit$^{CreERT2}$/IRG; Isl1-nLacZ embryo with arrows pointing to neural tube areas of X-gal and EGFP epifluorescence co-localization.

Neural crest cell fate-decisions are also dictated by Isl1, a homeobox gene that also specifies the majority of the mammalian cardiovascular cell lineages, including cardiac neural crest cells. However, Isl1-related pathways are thought to be distinct from cKit in the heart. To examine whether Isl1 is associated with NCC$^{kit}$ cardioblasts, cKit$^{CreERT2}$/IRG mice were crossed to mice carrying an Isl1 nuclear lacZ (nLacZ) knock-in allele. Pregnant mice were administered tamoxifen from 9.5-11.5 dpc. Embryos were harvested at 12.5 dpc and 14.5 dpc and expression of EGFP and nLacZ were assessed. Indeed, co-localization of EGFP and nLacZ was documented in cells of the neural tube, the dorsal root ganglion (DRG) and the OFT (data not shown). The majority of the EGFP/nLacZ double-positive cells in the neural tube and DRGs illustrated glial/neuronal cell specification, FIG. 6. Thus, Isl1 appears to be associated with NCC$^{kit}$ during cardioblastic lineage specification.

Figure 5:
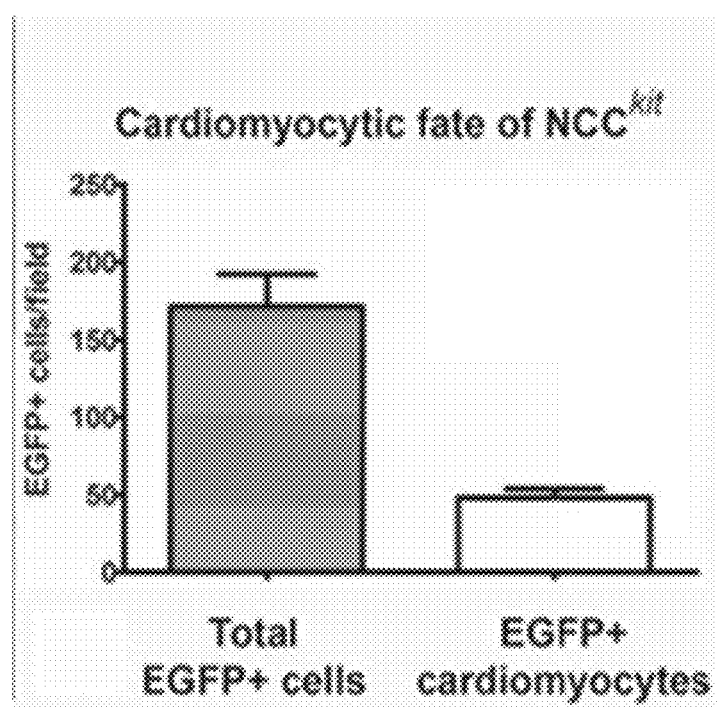
FIG. 5 shows the quantification of EGFP$^{(+)}$ cells and EGFP$^{(+)}$ cardiomyocytes in the heart of 18.5 dpc cKit$^{CreERT2}$/IRG embryo.

Confocal immunofluorescence analyses revealed that NCC$^{kit}$ contributed to all the expected lineages, including the tunica media of the aortic arch, outflow tract (OFT), cardiac and aortic valves and conduction system cells (data not shown). Contribution of NCC$^{kit}$ to endothelium and smooth muscle layers of the OFT was observed (data not shown), although coronary vascular cell differentiation was not observed (data not shown). However, a large number of atrial and ventricular cardiomyocytes (29.9%±3.1% of total EGFP$^{(+)}$ derivatives), as well as pericardial, endocardial and epicardial cells with robust EGFP or X-gal expression, FIG. 4 and FIG. 5, were unexpected for a role of cardiac NCC derivatives. Importantly, the majority of NCC$^{kit}$-derived cardiomyocytes were localized in the interventricular septum, FIG. 3, Panel E, FIG. 5.

To explore how the genetic fate-map compares to regular patterns of embryonic cKit antigen localization in heart, wild-type mouse embryos were examined. In agreement with our genetic findings in the cKit$^{CreERT2/+}$ allele, cKit immunohistochemistry revealed distinct populations of cells in multiple organs during embryogenesis of wild-type mice. Importantly, with this approach it was clearly detected a migration pattern of NCC$^{kit}$ lineage with a trajectory arising dorsally from the developing neural tube and dispersing ventrally and laterally toward the embryonic heart (data not shown). NCC$^{kit}$ appeared to gain myocardial access through the OFT, parietal pericardium and endocardium (data not shown).

Interactions between cardiac cKit and bone marrow-derived mesenchymal stem cells (MSCs) significantly improve the intrinsic regenerative response of the ischemic heart. Similar to other cKit$^{(+)}$ lineages, these interactions appear to be essential for propagating cKit$^{(+)}$ heart progenitors ex-vivo. Adult bone marrow may be an authentic source of postnatal neural crest cells; furthermore, ex-vivo expansion of tissue-specific progenitors for therapeutic use, was found to be enhanced in the presence of their original stroma.

Example 4

To study the mechanisms controlling migration and proliferation in postnatal cardiac NCC$^{kit}$ clones, 2-day old cKit$^{CreERT2}$/IRG neonates administered a single subcutaneous injection of 50 µl of tamoxifen. The next day, 3-day old postnatal hearts (PN3) were harvested, washed in ice-cold HBSS and cleaned from unwanted tissues under a stereomicroscope. They were then transferred in a tissue-cultured hood and, after additional washing steps with DMEM under sterile conditions, were minced into ~1 mm$^3$ fragments and digested in a solution of DMEM/F12, 20% FBS, 1% penicillin/streptomycin and 200 units/ml Collagenase-Type II solution at 37° C. Following that, tissue explants were collected and washed twice with DMEM. Single tissue fragments were then picked under a stereomicroscope using a pipette, and cultured individually in single wells of gelatin-coated 24-well plates, with or without 1×10$^5$ MSCs feeders. Samples were fed every other day. The basic myocardial explant feeding medium consisted of DMEM/F12, 15% FBS, 1% penicillin/streptomycin, 1% β-mercaptoethanol, 1000 units/ml recombinant mouse LIF, 1 ng/ml recombinant mouse bFGF, and 0.1 mM nonessential amino acids. The impact of SCF was tested by supplementing the medium with 100 ng/ml recombinant murine SCF. For cKit neutralization, 100 ng/ml of rat anti-murine cKit antibody were supplemented to the medium. For assessing the role of Sdf1/Cxcr4, AMD3100 was supplemented to the medium, at a final concentration of 1 µM. Samples were then monitored daily, and clonal growth of EGFP$^{(+)}$ cells was quantified every other day for 5-8 consecutive days, under a fluorescent microscope.

Myocardial explants from these animals were collected the following day, and were cultured in the presence or absence of MSC feeders. Swine MSCs were isolated and expanded from a single, healthy Yorkshire donor as previously described. Briefly, bone marrow was obtained from the iliac crest, and aspirates were passed through a density gradient to eliminate undesired cell types and were plated with 25 ml MEM Alpha media containing 20% fetal Bovine Serum in 162 cm$^2$ culture flasks. At 5-7 days after plating, non-adherent cells were washed away during medium changes and the remaining, plastic adherent, purified MSC population was expanded in culture. All used cells were harvested when they reached 80-90% confluence at passage 3-4, and inactivated for 3 h at 37° C. with 10 µg/ml of mitomycin C. Inactivated porcine MSC feeders were collected by trypsinization and cryopreserved in liquid nitrogen until use. For all experiments, MSCs feeders were seeded at a concentration of 2×10$^5$ MSCs/ml a day before use. The responses of EGFP$^{(+)}$ cells under different culture conditions were monitored daily and quantified via live-cell fluorescence imaging every other day.

Although the abundance of EGFP$^{(+)}$ cells after 5 days in culture was similar in the presence or absence of MSCs, MSCs were required for EGFP$^{(+)}$ cells to migrate outside of the tissue (data not shown). In the absence of MSCs, EGFP$^{(+)}$ cells remained strictly within the tissue borders. Moreover, co-culture with MSCs prevented spontaneous differentiation of EGFP$^{(+)}$ NCC$^{kit}$ into beating cells. These findings suggest that, unlike the endogenous EGFP$^{(-)}$/DsRed$^{(+)}$ postnatal cardiac stroma, MSCs support NCC$^{kit}$ migration.

Figure 7:
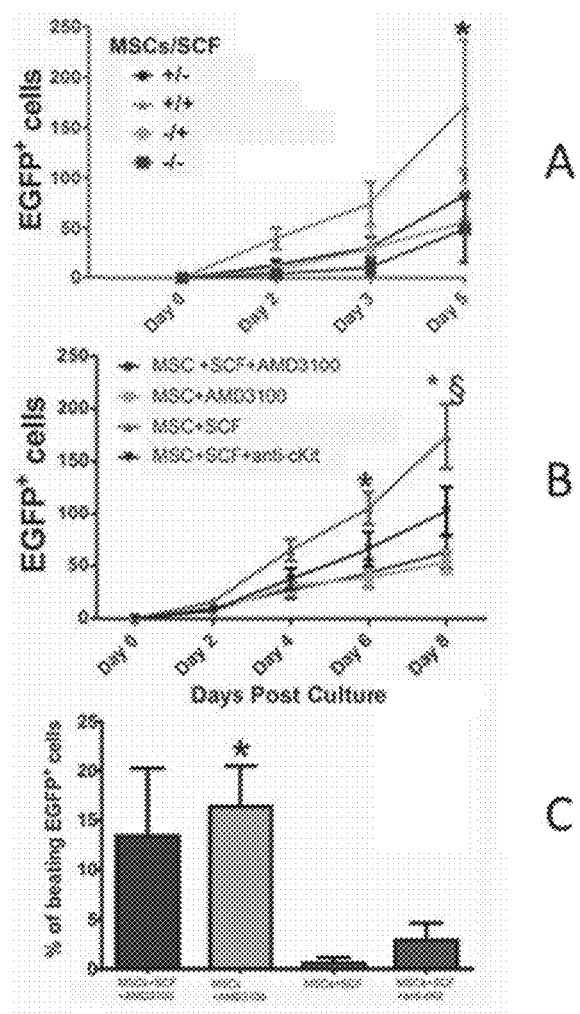
FIG. 7 shows a graph illustrating significant differences detected in the total number of EGFP$^{(+)}$ cells in the MSCs+SCF group (top line), compared to the other groups (*p<0.01) (A). Panel B illustrates that in addition to blocking cell migration, AMD3100 significantly decreased the number of EGFP$^{(+)}$ cells (*p<0.001), either in the presence (second from the bottom line) or absence (bottom line) of SCF, compared to the MSCs+SCF group (top line). Furthermore, neutralization of SCF/cKit signaling with anti-cKit antibody (second from the top line) significantly reduced the number of EGFP$^{(+)}$ cells compared to the MSCs+SCF group (top line), after 8 days in culture ($^\S$ p<0.001). Panel C illustrates the addition of AMD3100 caused a dramatic increase in the numbers of spontaneously beating EGFP$^{(+)}$ cells, compared to the other non-AMD3100 treated groups (*p<0001).
Figure 8:
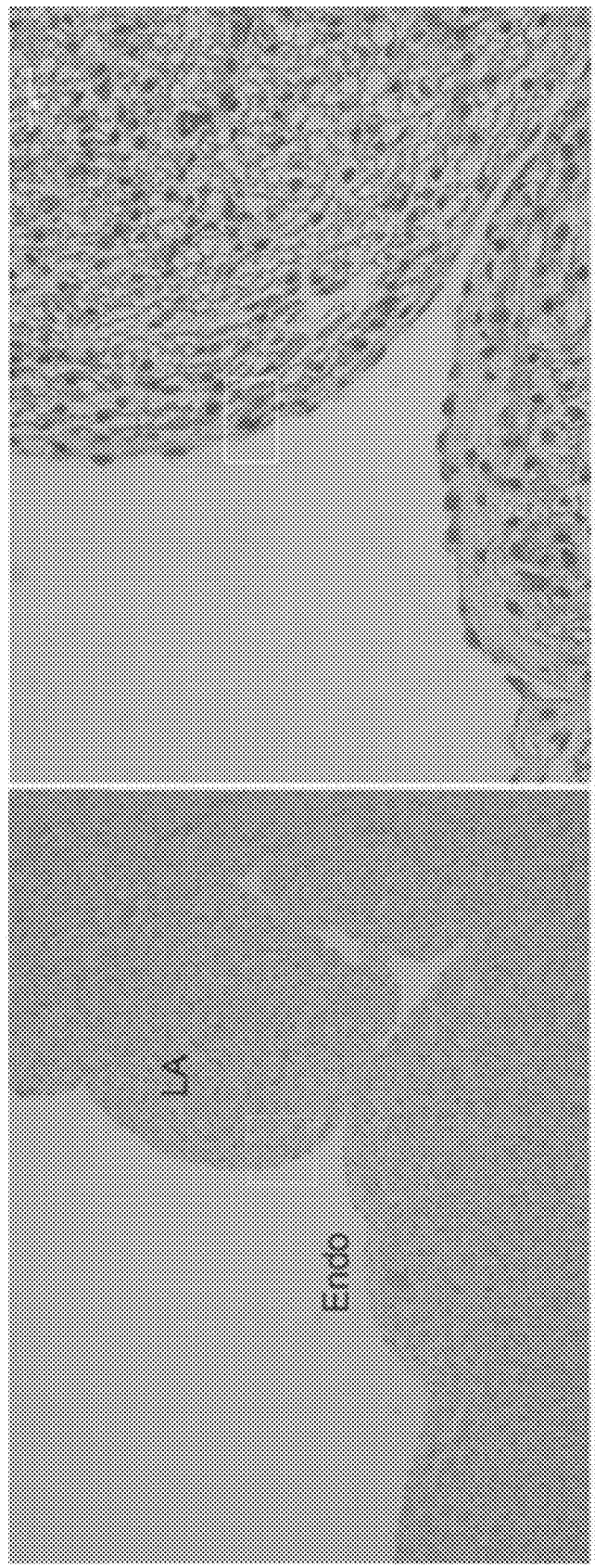
FIG. 8 shows hematoxylin-eosin staining illustrating a non-pigmented cKit$^{(+)}$/MITF$^{(+)}$ NCC$^{kit}$ (inset and arrow) in the endocardial surface of the left atrium, in a human fetal heart.

Consistent with the function of cKit in other lineages, expansion of adult cardiac cKit$^{(+)}$ cells is enhanced in the presence of SCF. Accordingly, to elucidate the role of SCF/cKit in mammalian NCC$^{kit}$ proliferation and migration, neonatal myocardial explants were cultured, as described above, in the presence or absence of recombinant murine SCF. Surprisingly, exogenous SCF increased by 3.5-fold the proliferative capacity of EGFP$^{(+)}$ cells, but only when MSCs were present, FIG. 7, Panels A-C. In the absence of MSCs, no significant differences were detected, suggesting that, as in other biological systems, SCF alone is not sufficient for supporting NCC$^{kit}$ proliferation. Similarly, neutralization of SCF/cKit signaling with an anti-cKit antibody prevented the effects of SCF on NCC$^{kit}$ proliferation. However, neither SCF nor cKit affected EGFP$^{(+)}$ cell migration (data not shown). Thus, SCF/cKit signaling regulates the proliferative but not the migratory capacity of NCC$^{kit}$.

Example 5

The effect of MSCs on NCC$^{kit}$ migration was explored because recent studies reveal a chemotactic role of Sdf1/Cxcr4 axis on NCCs. Myocardial explant cultures were generated, as described above, and screened the emergence of EGFP$^{(+)}$ cells in response to AMD3100, an inhibitor of the Sdf1/Cxcr4 axis. As expected, AMD3100 blocked the migration of EGFP$^{(+)}$ cells from the cultured explants (data not shown). Strikingly, AMD3100 caused a significant reduction in the abundance of EGFP$^{(+)}$ cells while causing their massive differentiation into spontaneously contracting cardiomyocytes (data not shown). Thus, Sdf1/Cxcr4 axis regulates migration and differentiation of NCC$^{kit}$.

Example 6

To determine whether NCC$^{kit}$ is part of the human cardiopoietic program and cells with a similar phenotype to murine NCC$^{kit}$ were present in the developing human heart, confocal immunofluorescence analysis of cKit was carried out and demonstrated a mean of 1178±142 NCC$^{kit}$/cm$^3$ dispersed throughout the outflow tract, epicardial, endocardial, compact myocardial and perivascular walls. Consistent with the murine cardiac NCC$^{kit}$ phenotype, human NCC$^{kit}$ co-expressed Mitf and Isl1 as well as Connexin-43, a gap junction protein that identifies cardiac NCC lineages during murine cardiogenesis (data not shown).

NCC$^{kit}$ expressing cells were isolated from human fetal hearts (15-22 weeks of gestation) using the primary explants technique described above. Briefly, human fetal hearts were kept in cold Hank's Balanced Salt Solution containing 1% penicillin/streptomycin until processing. After washing thoroughly with DMEM, samples were minced in ~1 mm$^3$ fragments and digested in a solution of DMEM/F12, 20% FBS, 1% penicillin/streptomycin and 200 units/ml Collagenase-Type II solution at 37° C. Whole cell lysates and tissue explants were then collected, washed twice with DMEM, resuspended in ECM medium (DMEM/F12, 15% FBS, 1% penicillin/streptomycin, 1% beta-mercaptoethanol, 1000 units/ml recombinant human LIF, 100 ng/ml recombinant human SCF, 10 ng/ml recombinant human bFGF, and 0.1 mM nonessential aminoacids) and seeded in gelatin coated 6-well plates containing 0.4×10$^6$ MSC feeder cells per well. After 7-10 days, samples were collected by trypsinization and cKit$^{(+)}$ cells were magnetically purified using an APC-conjugated monoclonal anti-human cKit antibody and 5 consecutive cycles of magnetic cell sorting. Purified NCC$^{kit}$ were then expanded with ECM medium on MSC feeders for multiple passages. Subsequent immunocytochemical evaluation was performed on cytospin preparations.

Example 7

Ex-vivo the properties of human fetal NCC$^{kit}$ were tested. Human fetal myocardial explants were seeded on MSC feeders, and cultured for 7-10 days with recombinant human SCF (data not shown). NCC$^{kit}$ were isolated using an antibody specific to the human cKit (data not shown). Purified cells had a non-pigmented, spindle-shaped morphology and were subcultured on MSCs feeders for multiple passages. Immunophenotypic analyses of the expanded clones documented that over 80% of the human NCC$^{kit}$ expressed Isl1, Mitf, and Connexin-43, as well as the cardiac transcription factors Gata4 and Nkx2-5 (data not shown). Consistent with our previous reports, expression of Kdr, a VEGF receptor, was not documented. Single-cell gene expression analysis was performed via multiplex RNA in-situ hybridization. Transcripts of cKit, Isl1, Nkx2-5 and Gata-4 were abundantly co-expressed within single NCC$^{kit}$ clones (data not shown). Notably, Isl1 transcripts accumulated within the nucleus of NCC$^{kit}$ suggesting important nucleoplasmic properties and gene-transcription mechanics of the fetal human cardiac NCC.

Example 8

In-vitro differentiation capacity of NCC$^{kit}$ was tested in a co-culture system with neonatal rat cardiomyocytes (NRCMs). Briefly, NRCMs were isolated and plated at a density of 1.5×10$^5$ NRCMs/cm$^2$ in gelatin-coated 12-well plates. NCC$^{kit}$ were then co-cultured with NRCMs in a 1/10 ratio, indirectly using transwell insets with a 0.4 μm pore size. Co-cultures were maintained with NRCM medium consisting of IMDM glutamax, 10% FBS, insulin-transferrin-selenite, 1% bovine serum albumin, 20 μg/ml ascorbic acid, 1% penicillin-streptomycin, and incubated for up to 2 weeks in humidified incubator at 37° C. and 5% CO$_2$. For immunocytochemical evaluation, cells were fixed in 4% paraformaldehyde for 20 min at RT. For differentiation into pigmented melanocytes, NCC$^{kit}$ were cultured as spheres in ultra-low attachment 6-well plates and fed with IMDM glutamax, 20% FBS, 1% penicillin-streptomycin, 1% non-essential amino acids and monothioglycerol.

Figure 9:
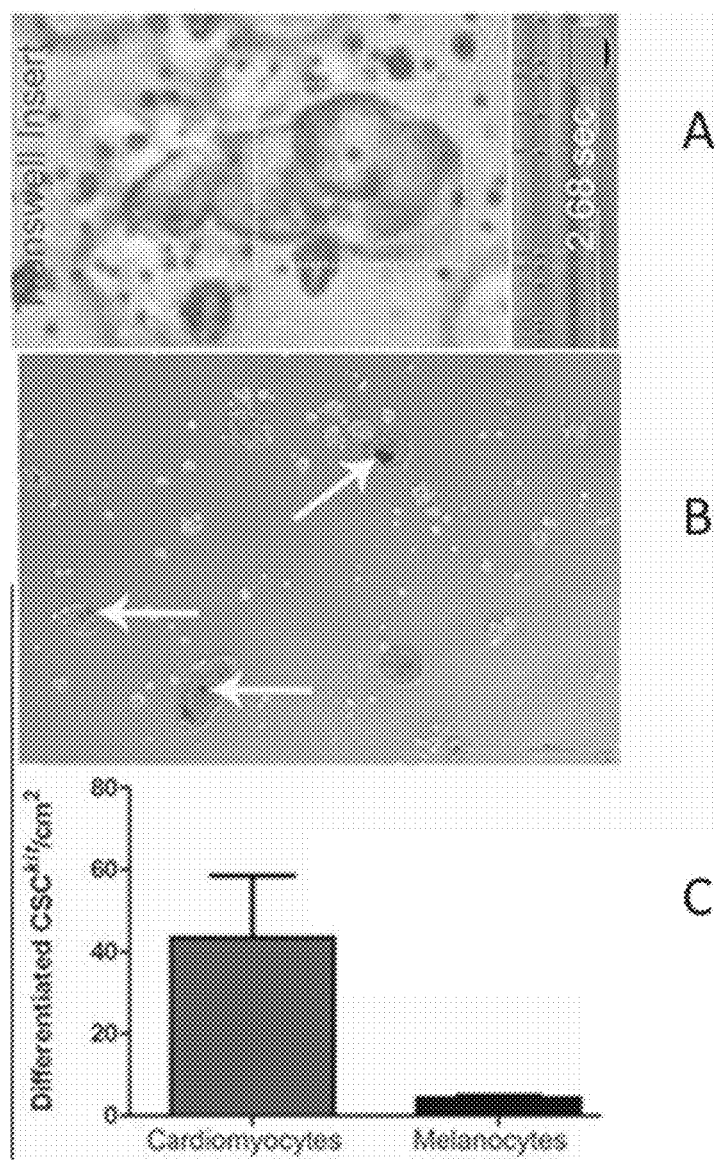
FIG. 9 shows a human NCC$^{kit}$ that contracts spontaneously 11 times during a 2.68 second period of time (A); differentiation of NCC$^{kit}$ into Tyrosinase$^{(+)}$ melanocytes, substantiates the laterally-migrating NCC origins of NCC$^{kit}$ (B); quantification of cardiomyocytic vs. melanocytic derivatives in the co-culture system illustrated a mean of 43.1±14.7 cells/cm$^2$ and 4.3±0.6 cells/cm$^2$ respectively (n=24) (C).
Figure 10:
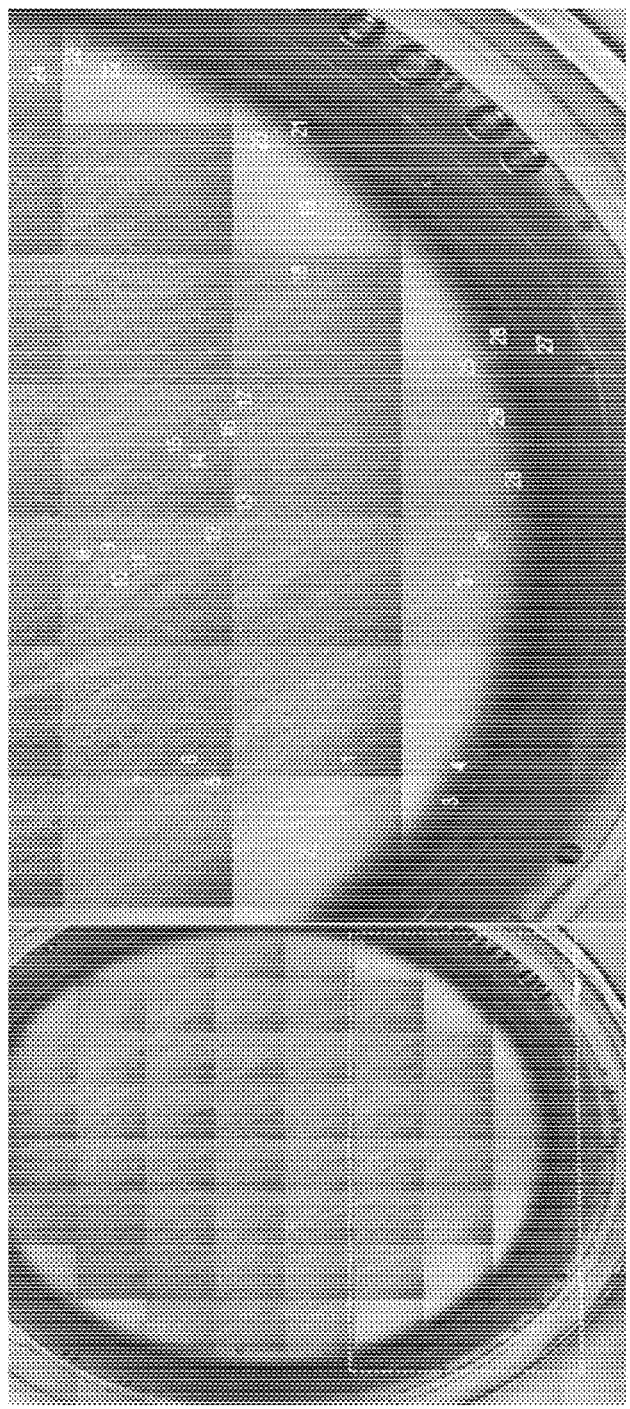
FIG. 10 shows a confocal tile-scan of a transwell inset containing NCC$^{kit}$ 12 days after co-culture with NRCMs. In this particular plane, 31 cardiac troponin-I$^{(+)}$ (red), spontaneously contracting NCC$^{kit}$-derived human cardiomyocytes are shown.

After ~4 days in culture, spontaneously contracting progeny of culture expanded NCC$^{kit}$ were recorded, FIG. 9 and FIG. 10. Confocal immunofluorescence analyses illustrated full differentiation into GATA4$^{(+)}$, cardiac Troponin-I$^{(+)}$ and Tropomyosin$^{(+)}$ striated human cardiomyocytes. Calponin and α-smooth muscle actin expression, indicated capacity for vascular smooth muscle cell differentiation. Additionally, NCC$^{kit}$ expressed Connexin-43 and differentiated into Neurofilament$^{(+)}$ conduction system cells as well as pigmented, Tyrosinase$^{(+)}$ melanocytes, FIG. 9 and FIG. 10. In contrast, Factor-VIII$^{(+)}$ or KDR$^{(+)}$ progeny were not detected ex-vivo, indicating lack of in-vitro NCC$^{kit}$ differentiation into endothelial lineages, FIG. 9, Panels A-C.

Example 9

Heart development is a highly-regulated process under which cell lineage diversification and growth programs are dynamically coordinated, in a time- and space-dependent manner. These programs are activated sequentially, in parallel or intersect to give rise to distinct domains of the heart. For example, the myocardial lineage originally develops from progenitors of the cardiogenic mesoderm. However, later during heart morphogenesis, hemogenic endothelium progenitors, epicardial progenitors, cardiopulmonary progenitors, CNC progenitors and proliferating cardiomyocytes, will converge to systematically contribute new cardiomyocytes. Gauging the relative contribution of each lineage for scaling their cardiomyogenic- and consequently therapeutic-capacity is a challenging task. First, because many of these lineages are heterogeneous and incompletely characterized, and therefore cannot always be traced under a straight-forward genetic-fate mapping experiment. And second, because it is unknown how influential the changes in the cardiac milieu (i.e. morphogen gradients, tissue composition, tissue size) are in determining the final proportions of heart muscle derived from each lineage.

Recently, a straightforward genetic fate-mapping study showed that a relatively small proportion of the mouse myocardium is derived from a cardiac progenitor lineage expressing cKit, and therefore suggested that their cardiomyogenic capacity may be functionally insignificant. However, the identity of the cardiomyogenic cKit$^+$ cells and the mechanisms controlling their differentiation into cardiomyocytes remain unknown. Here, by employing a high-resolution genetic lineage-tracing strategy, followed by an iPSC-based model of mouse cardiogenesis, it was demonstrated that cKit marks cardiac neural crest progenitors; and show that their limited contribution to myocardium is not related to poor cardiomyogenic capacity, but to changes in the activity of noggin-mediated BMP antagonism in the cardiac milieu, which drives their differentiation into cardiomyocytes.

Genetic Lineage-Tracing of cKit$^+$ Heart Progenitors.

A well-characterized, inducible cKit$^{CreERT2/+}$ mouse line was employed to trace the lineage of cKit$^+$ heart progenitors. cKit$^{CreERT2/+}$ mice were generated by homologous recombination as a knock-in of a CreER$^{T2}$ expression cassette into the ATG start codon at the endogenous cKit locus, as recently described. Consistent with other heterozygous cKit mutants, cKit$^{CreERT2/+}$ are healthy and fertile, and characterized by the white spotting phenotype (FIG. 11, Panels A-B).

Figure 11:
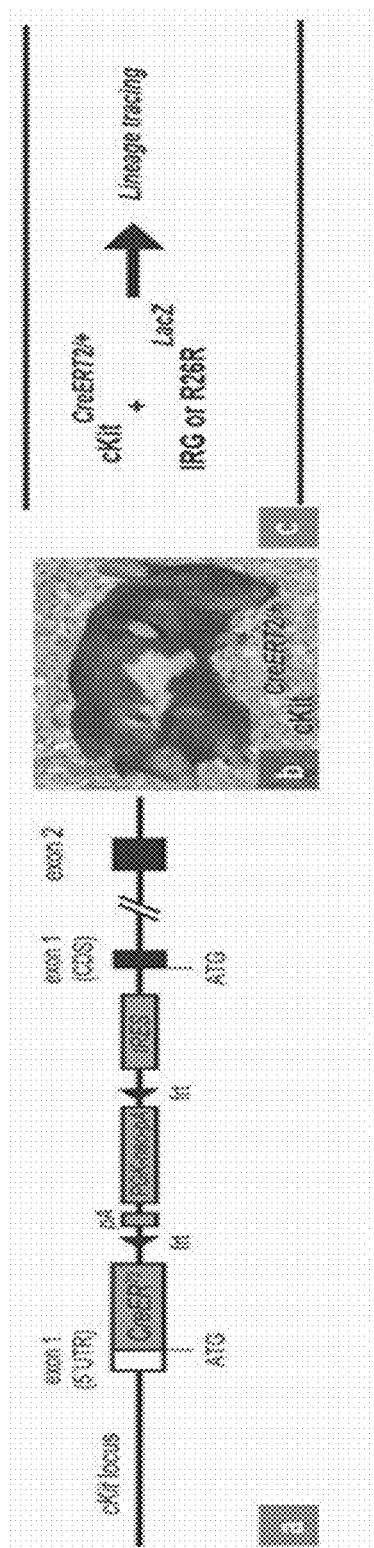
FIG. 11 shows cKit$^{CreERT2/+}$ genetic fate-map revealing a novel cardiac NCC lineage; schematic of the CreER$^{T2}$ knock-in allele; UTR: untranslated region, CDS: coding sequence (A); phenotype of cKit$^{CreERT2/+}$ mice (B); study design (C); Lineage-tracing in the cKit$^{CreERT2}$/R26R$^{lacZ}$ alleles, 500 pixels (D-G); summary of cKit genetic fate-map (H).
Figure 11:
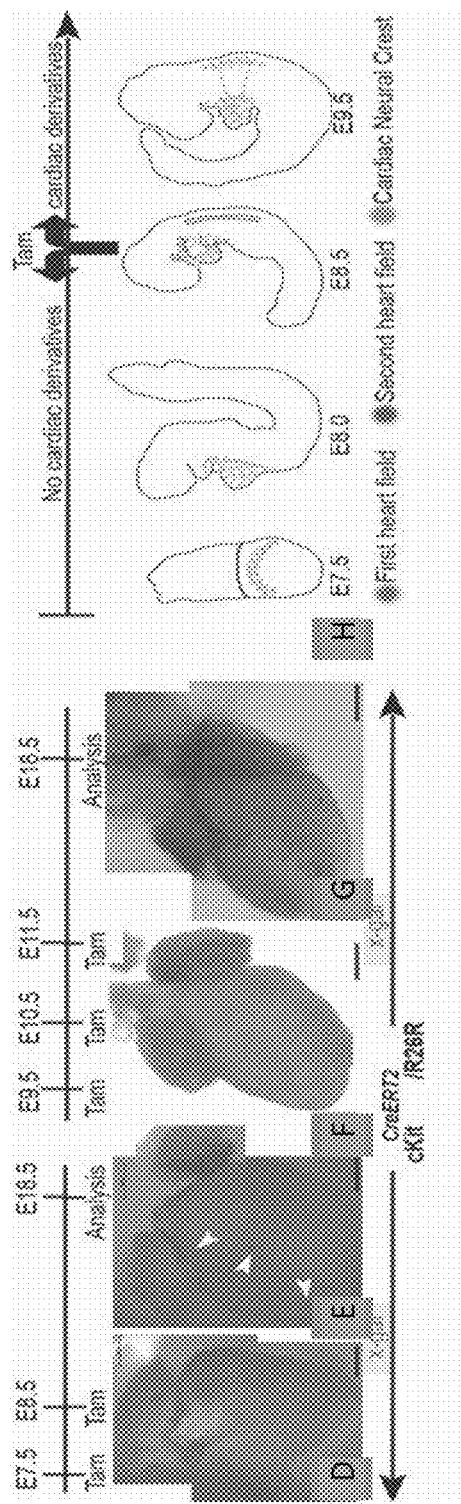

Genetic lineage-tracing of cKit expressing cells was performed by crossing cKit$^{CreERT2/+}$ mice to two previously established Cre-reporter mouse lines; the dual fluorescent color-reporter DsRed/EGFP (IRG) or the beta-galactosidase-reporter $R26R^{lacZ}$ (FIG. 11, Panel C).

It was first interrogated whether cKit marks first or second heart-field myocardial progenitors, by administering pregnant mice carrying $cKit^{CreERT2}$/IRG embryos with tamoxifen from embryonic days E7.5 to E8.5. Thus, cells actively expressing cKit during this period, and their progeny, were irreversibly labeled with EGFP. Embryos were collected at E18.5, and EGFP expression was assessed via live-tissue imaging, as well as confocal epifluorescence and immunofluorescence analyses in fixed samples. Consistent with previous reports on embryonic cKit expression, successful recombination was reflected in robust EGFP expression in circulating blood cells, testes and lungs (data not shown). However, in contrast to others, expression of $EGFP^{(+)}$ in the heart was only rarely detected. These rare $EGFP^{(+)}$ cells were non-cardiomyocytes, which occasionally co-localized with the cardiac transcription factor Gata4 (data not shown). Thus, our findings do not support the existence of a $cKit^+$ cardiac stem/progenitor cell lineage in the cardiogenic mesoderm, as has been previously suggested.

It was next tested whether cKit marks other cardiomyogenic lineages, such as proliferating cardiomyocytes, progenitors of the proepicardial organ, progenitors of the hemogenic endothelium and endocardium, cardiopulmonary progenitors, and cardiac neural crest progenitors. Accordingly, since these lineages develop subsequently to cardiac mesodermal progenitors, it was administered tamoxifen to pregnant mice at selected time-points during E9.5-E12.5. $cKit^{CreERT2/+}$ mediated recombination resulted in the expression of lineage tracers in embryonic melanoblasts, craniofacial region, neural tube, dorsal root ganglia (DRGs), circulating blood cells, gastrointestinal cells, testicular [data not shown] and pulmonary cells (data not shown). Strikingly, in contrast to the genetic fate-map of E7.5-E8.5 cKit-expressing cells, robust EGFP epifluorescence was consistently detected within the cardiac outflow tract (OFT), epicardium and myocardium in all of the live, beating Cre-recombined E18.5 $cKit^{CreERT2}$/IRG embryonic hearts examined (data not shown).

Because Cre-mediated genetic fate-mapping has been reported to vary significantly between different Cre-reporter alleles, often leading to misinterpretation of data, it was investigated whether similar flaws could underlie the analysis with the $cKit^{CreERT2/+}$ and IRG alleles. It was therefore replicated our fate-mapping strategy, using the $cKit^{CreERT2}$/$R26R^{lacZ}$ mice. Histological assessment of the genetic fate-maps with X-gal revealed that recombination in $cKit^{CreERT2}$/$R26R^{lacZ}$ embryos produced similar mosaic patterns to $cKit^{CreERT2}$/IRG (FIG. 11, Panels D-G). Thus, tamoxifen-induced Cre-recombination is specific for the cKit lineage and consistent between different lox-stop-lox silenced reporter-alleles.

It was next sought to identify the original population of cells that were being labeled by the $cKit^{CreERT2/+}$ lineage tracers. Accordingly, timed-pregnant mice were administered tamoxifen at selected time points between E9.5-E13.5, and embryos were collected 24 h after the last injection. Immunohistochemical analysis confirmed the expression of cKit in cells expressing the cre lineage tracers. Using live epifluorescence and confocal immunofluorescence imaging it was detected that recombination occurred in the neural tube, melanocytes, lungs, gut, outflow tract, epicardium, and atrioventricular junctions, but not within the myocardium. Thus, the origin of the $cKit^{CreERT2/+}$-labeled heart cells during the period of tamoxifen-induced recombination is not the myocardium (i.e. differentiated cardiomyocytes or trans-differentiating cardiac fibroblasts), and therefore the $cKit^{CreERT2/+}$ myocardial progeny are derived from an extra-cardiac progenitor lineage.

Last, since the $cKit^{CreERT2/+}$ allele is non-functional, it was examined for possible differences in the expression of cKit between embryos carrying $cKit^{CreERT2/+}$ or $cKit^{+/+}$ alleles. Consistent with previous reports, confocal immunohistochemistry showed no apparent differences in the expression of cKit between the two strains. Similar to the $cKit^{CreERT2/+}$ lineage tracers, cKit expressing-cells were localized in the neural tube, melanocytes, lung, the OFT and epicardium, but not in the myocardium of $cKit^{+/+}$ embryos.

Thus, collectively, our lineage-tracing studies delineate that cKit marks a heart cell lineage which emerges at ~E9.5 and contributes consistently to the development of the mouse heart.

Intersectional Genetic Fate-Mapping of cKit and Wnt1.

The expression of $cKit^{CreERT2/+}$ lineage tracers in the neural tube, skin, lung, gut and heart, is more consistent with the hypothesis that cKit marks progenitors of the CNC lineage. Furthermore, the white spotting phenotype of $cKit^{CreERT2/+}$ mice (FIG. 11, Panel B), similar to other cKit mutants, implies impaired melanogenesis, and therefore, highlights the important role of cKit in neural crest pathways. Consequently, it was sought to elucidate whether cKit delineates cells of CNC lineage.

First, utilized was a neural crest-specific mouse line, the $Wnt1-Cre/R26^{tdTomato}$, in which early-migrating CNCs and their derivatives are irreversibly labeled by the red fluorescence protein tdTomato. Confocal immunohistochemistry against cKit illustrated its co-localization with tdTomato in various tissues of E12.5 $Wnt1-Cre/R26^{tdTomato}$ embryos, including the neural tube and the heart, further suggesting the neural crest as the origin of $cKit^+$ cardiac progenitors.

However, since the Wnt1-Cre and $cKit^{CreERT2/+}$ driver lines are not suitable by themselves for multiplex lineage-tracing studies to genetically interrogate whether the $cKit^{CreERT2/+}$ cardiac progeny truly originate from $Wnt1^+$ CNCs, a novel a mouse line carrying two recombinase systems (Cre-loxP and Flp-FRT) was generated and therefore enables intersectional genetic fate-mapping of $cKit^{CreERT2/+}$ in the Wnt1-expressing CNC lineage and its derivatives. A previously established dual-recombinase responsive indicator allele, the RC::Fela and a novel Flpe recombinase driver line, Wnt1::Flpe4351 were utilized. The RC::Fela activates expression of EGFP upon Flpe-mediated recombination, and nuclear β-galacotisdase (nLacZ) when both Cre and Flpe recombinases are expressed. The Wnt1::Flpe4351 mediates Flpe recombination in Wnt1-expressing CNCs. Placing the RC::Fela and Wnt1::Flpe4351 in combination with the $cKit^{CreERT2/+}$ allele ($cKit^{CreERT2}$;$Wnt1^{Flpe}$; RC::Fela), allowed us to generate and analyze the intersectional genetic fate-map of cKit and Wnt1 in the developing mouse heart, and therefore genetically trace whether cKit is truly a marker of the cardiac CNC lineage.

Figure 12A:
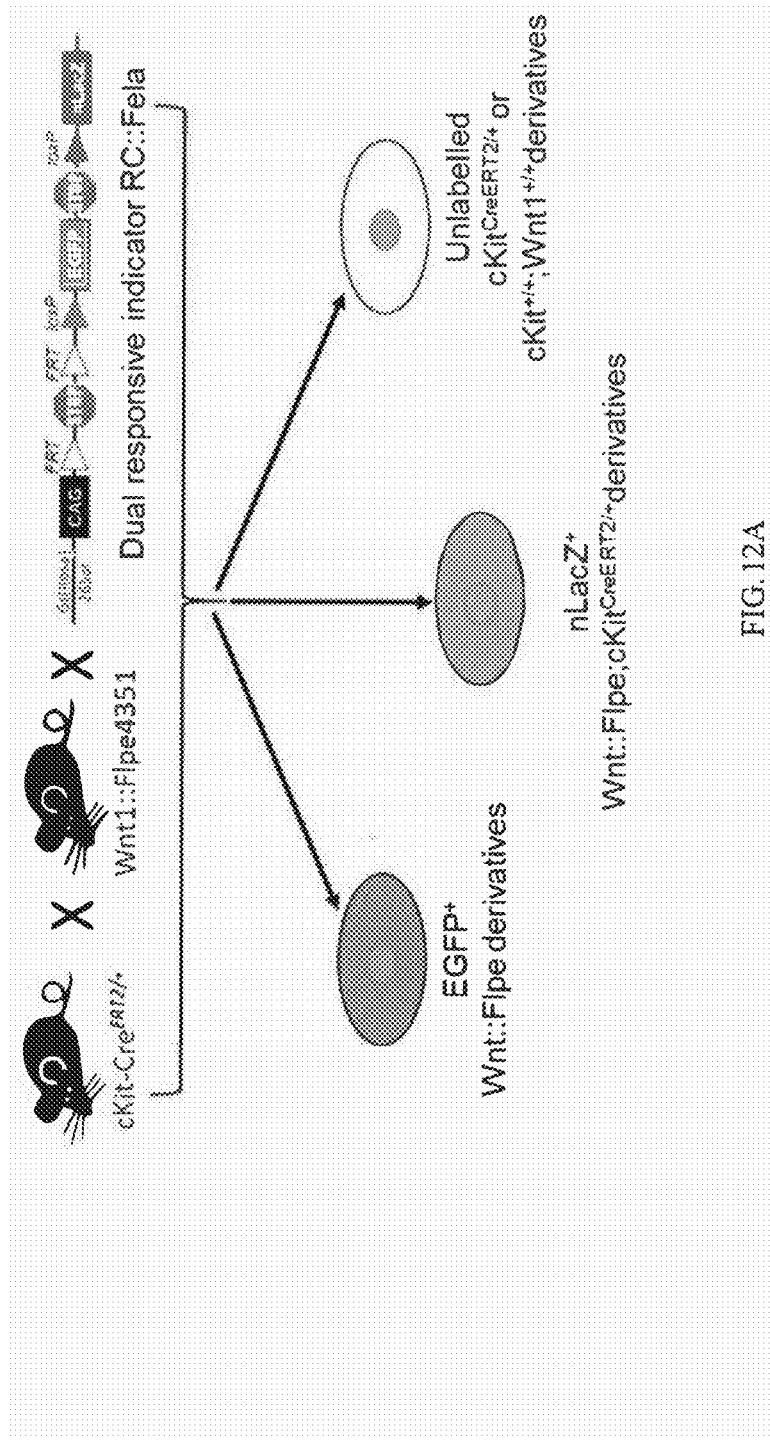
FIG. 12 shows high-resolution intersectional genetic fate-mapping of cKit and Wnt1 and a schematic of the intersectional genetic fate mapping strategy (Panel A); x-gal staining demonstrating absence of beta-galactosidase expression, scale bar=500 μm (Panel B); x-gal staining demonstrates expression of x-gal in the heart of tamoxifen-treated cKit$^{CreERT2}$;Wnt1::Flpe;RC::Fela embryos (Panel C).
Figure 12B:
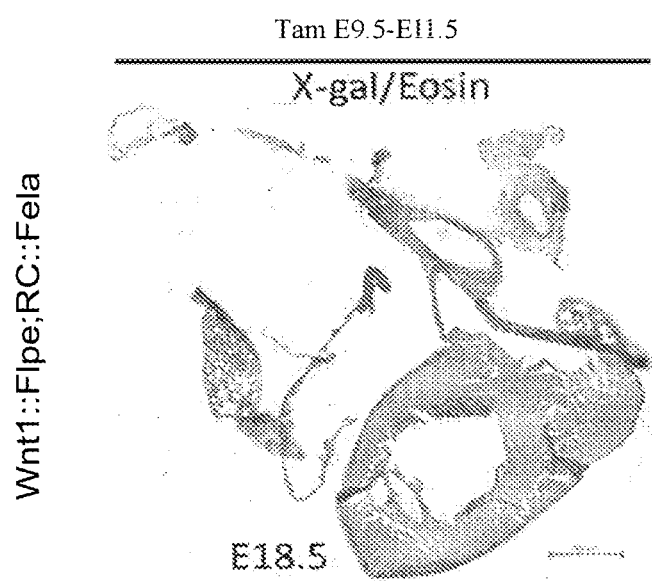
Figure 12C:
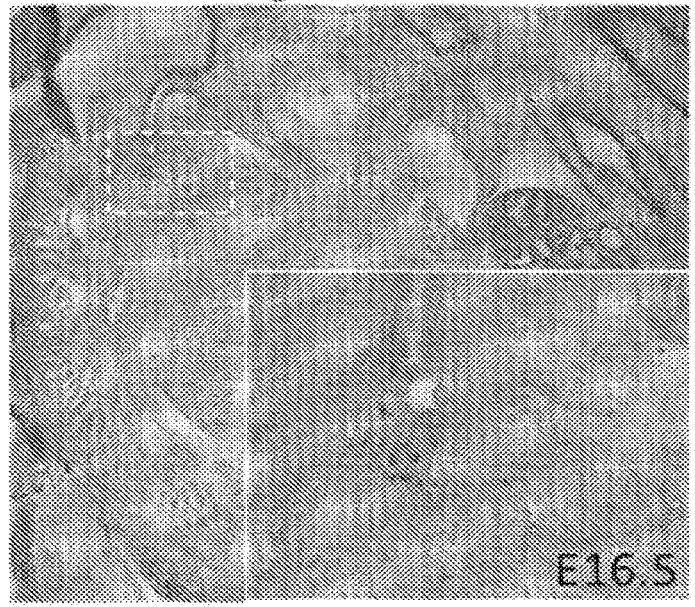

To specifically analyze the expression of cKit in Wnt1-expressing neural crest cells, timed-pregnant mice carrying $cKit^{CreERT2}$;$Wnt1^{Flpe}$;RC::Fela embryos were administered tamoxifen during E9.5-E11.5 and embryo analysis was performed at E16.5-E18.5. Consistent with previous studies, expression of EGFP and nLacZ were undetected in embryos which did not express Flpe and Cre (data not shown). Similar to other Wnt1-reporter mouse lines, when Wnt1::Flpe4351 was expressed in the presence of RC::Fela, robust EGFP epifluorescence and immunofluorescence was detected in the craniofacial region, melanocytes, DRG, lungs, OFT, as well as in cells within the epicardium and myocardium (FIG. 12, Panels A-C). Expression of nLacZ was not detected. When both Wnt1::Flpe4351 and cKit$^{CreERT2/+}$ were expressed, EGFP expression persisted in all neural crest derived tissues, including the heart and OFT. However, consistent with our cKit$^{CreERT2}$/IRG and cKit$^{CreERT2}$/R26R$^{lacZ}$ genetic lineage-tracing data, robust nLacZ expression was also seen in the craniofacial region, melanocytes, DRG, gut, OFT, as well as in cells within the epicardium and myocardium (FIG. 12, Panels A-C). Thus, our intersectional genetic fate-mapping studies indicate that cKit marks a subpopulation of the Wnt1-expressing progenitors (CNC$^{kit}$) in the cranial, cardiac, vagal, sacral and trunk neural crest lineages and, therefore, illustrate that cKit$^+$ cardiac progenitors are of neural crest origin.

CNC$^{kit}$ derivatives. The identity of the CNC$^{kit}$ derivatives was characterized via confocal immunofluorescence analyses. Lineage tracers were expressed in all the expected cardiac neural crest derivatives, including OFT (FIGS. 11, 12, & 13), the tunica media of the aortic arch (FIG. 13), cardiac and aortic valves (FIG. 13), atria (data not shown), inflow tract, satellite glial progenitors and sensory cells. Consistent with their neural crest origin, CNC$^{kit}$ contributed to endothelium and smooth muscle layers of the OFT (FIG. 13), although coronary vascular cell differentiation was not observed (FIG. 13).

Figure 13:
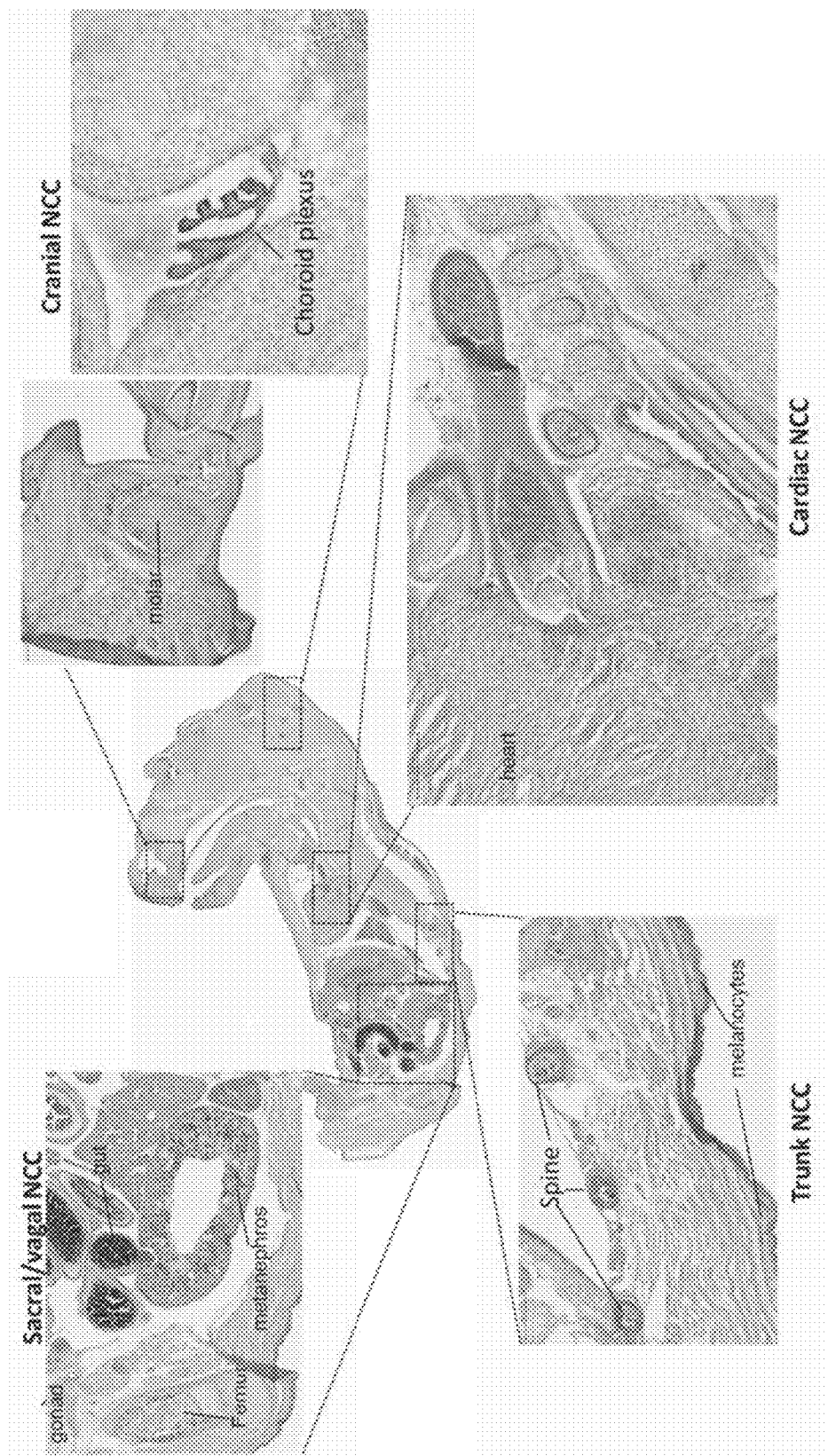
FIG. 13 shows the segregation of the NCC$^{kit}$ lineage in the mouse embryo; representative x-gal stained section illustrating the segregation of the NCC$^{kit}$ lineage in E16.5 cKit$^{CreERT2}$;Wnt1::Flpe;RC::Fela embryos; detection of x-gal is documented in the craniofacial region, heart, spine, skin, gut and kidney. Thus, NCC$^{kit}$ contribute to all known neural crest lineages (cranial, cardiac, vagal, sacral, trunk); tamoxifen was administered during E9.5-E11.5; scale bars=200 μm.

Last, in agreement with previous reports in zebrafish and mice, it was consistently documented contribution to atrial and ventricular cardiomyocytes [29.9%±3.1% of total EGFP$^{(+)}$ derivatives (FIG. 13), as well as pericardial, endocardial and epicardial cells (FIG. 11 and FIG. 13). Importantly, the majority of CNC$^{kit}$-derived cardiomyocytes were localized in the interventricular septal wall (FIG. 28K and FIG. 30).

Figure 14:
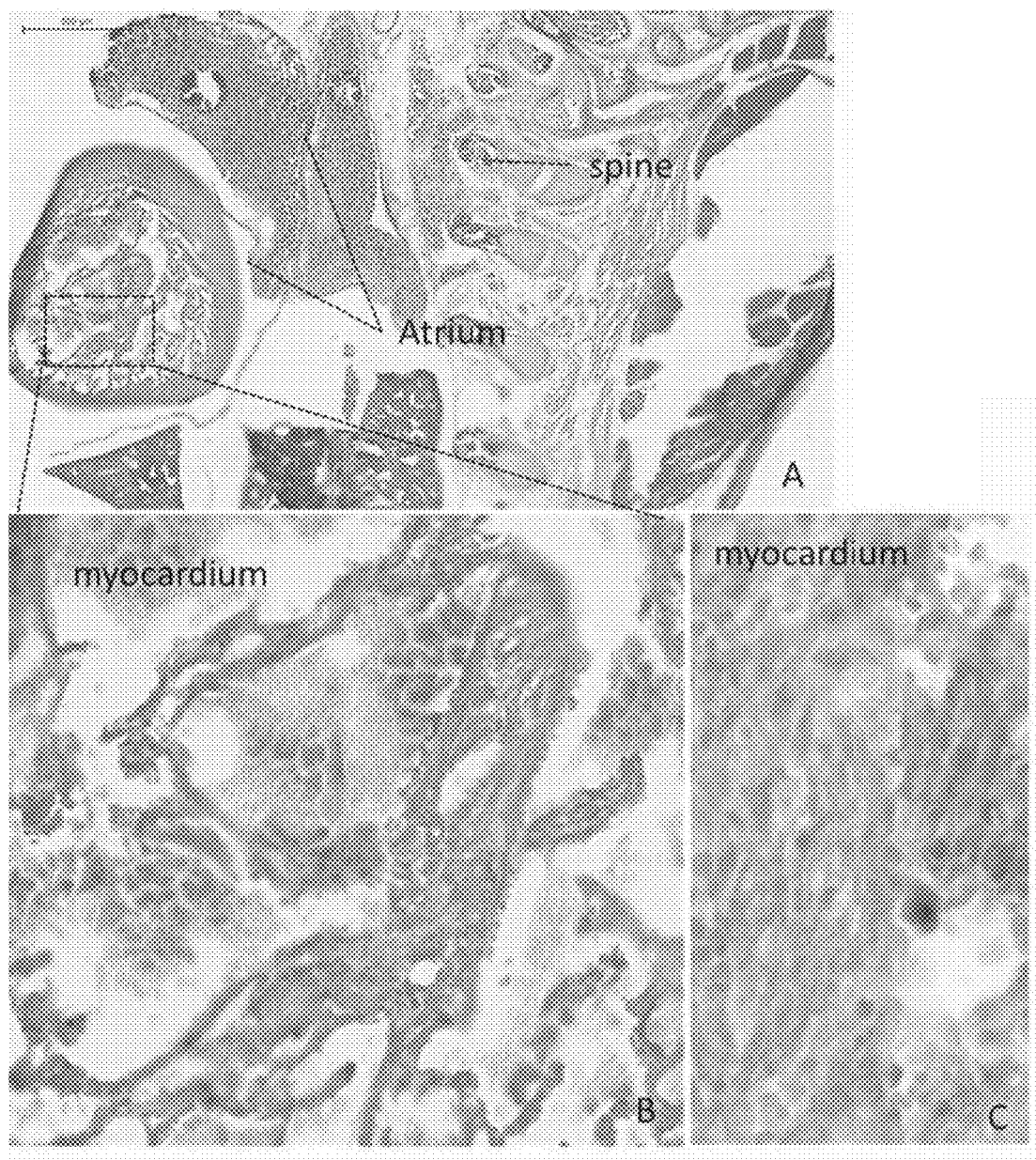
FIG. 14 shows the segregation of the cardiac NCC$^{kit}$ lineage in the mouse heart; x-gal$^+$ staining in E16.5 cKit$^{CreERT2}$;Wnt1::Flpe;RC::Fela heart following tamoxifen (Tam) administration during E9.5-E11.5. NCC$^{kit}$ contribute to all the expected cardiac NCC derivatives including the myocardium, atria (A-C), epicardium (D), endocardium (E), outflow (F) and inflow (G) tract.
Figure 15:
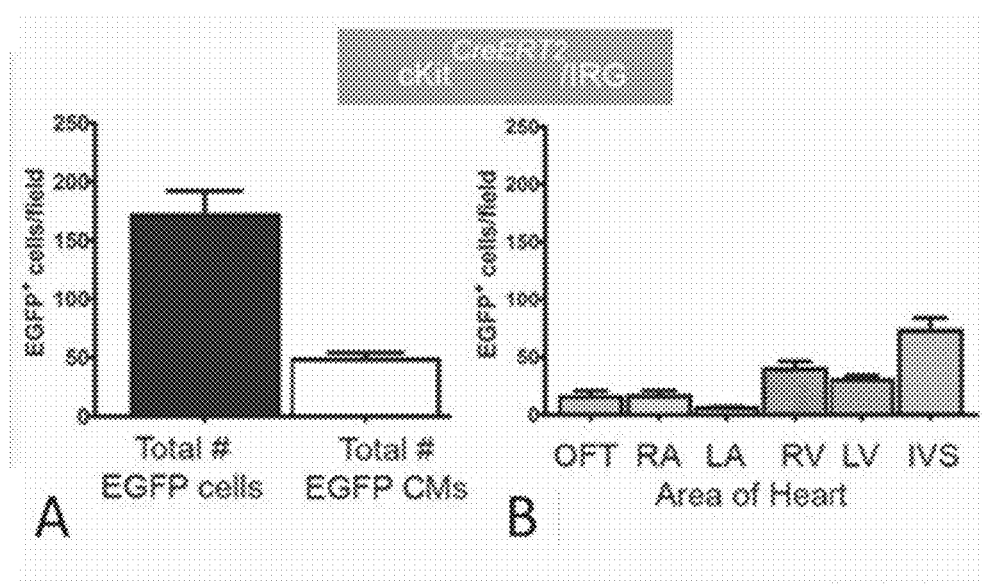
FIG. 15 shows cardiomyocytic versus non-cardiomyocytic EGFP$^{(+)}$ derivatives in the heart (A); distribution of EGFP$^{(+)}$ cells in the heart [n=11 cryosections from 3 embryos (A & B). Acronyms in FIG. 32 include outflow tract (OFT); left atrium (LA); aortic valve (AoV); mitral valve (MV); left ventricle (LV); right ventricle (RV); interventricular septum (IVS); cardiomyocytes (CM).
Figure 16A:
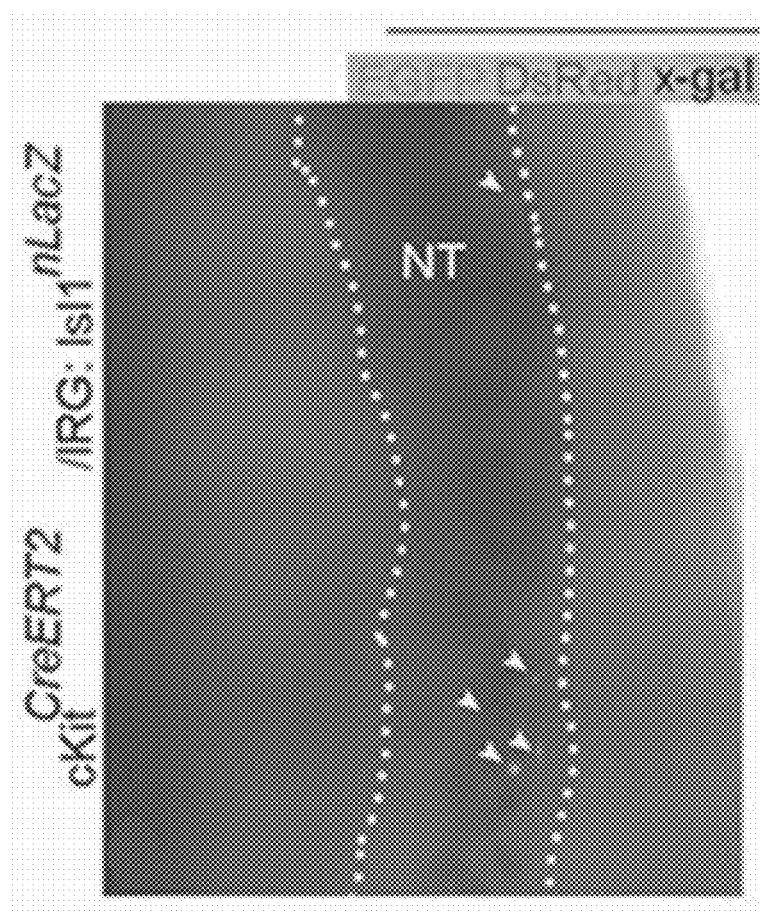
FIG. 16A shows co-localization of x-gal and EGFP epi-fluorescence in cKit$^{CreERT2}$/IRG:Isl1$^{nLacZ}$ embryos.
Figure 16B:
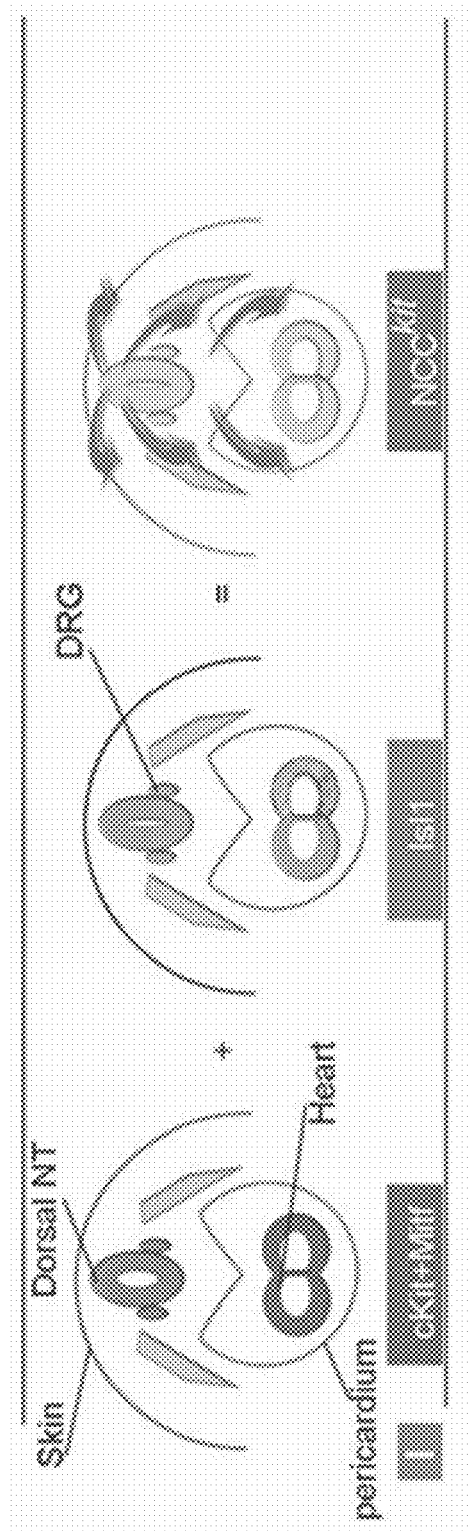
FIG. 16B shows a schematic illustrating the phenotype of NCC$^{kit}$.

CNC$^{kit}$ identity. To better characterize the original identity of cardiac CNC$^{kit}$, the expression of Isl1, a homeobox transcription factor that specifies the majority of the mammalian cardiovascular cell lineages, including cardiac CNCs was studied. Accordingly, cKit$^{CreERT2}$/IRG mice were crossed to mice carrying an Isl1 nuclear lacZ (Isl1$^{nLacz}$) allele. Subsequently, pregnant mice were administered tamoxifen from E9.5-E11.5, and expression of EGFP and Isl1$^{nLacz}$ were assessed in E12.5 embryos. Indeed, co-localization of EGFP and nLacZ was documented in cells of the neural tube, the dorsal root ganglion (DRG) and the OFT (FIGS. 13-14). Consistent with previous reports, EGFP/Isl1$^{nLacz}$ double-positive cells in the neural tube and DRGs illustrated specification to glial/neuronal cell lineages (FIGS. 13-14).

Next, the expression of micropthalmia-associated transcription factor (Mitf), perhaps the best characterized target and transactivator of cKit signaling, and a known marker for cranial neural crest derivatives, mast cells, but also cardiomyocytes was investigated. Confocal immunofluorescence analysis demonstrated that Mitf is also expressed in CNC$^{kit}$ and their cardiomyocytic derivatives (data not shown). However, EGFP$^+$ cells in the heart did not express the melanocyte-specific markers tyrosinase or trp1 demonstrating that Mitf$^+$ CNC$^{kit}$ derivatives in the heart are not melanocytes (FIG. 14, Panel D).

BMP Inhibition Induces Cardiomyogenesis in CNC$^{kit}$.

Our genetic fate-mapping data show that cKit$^+$ progenitors consistently contribute a small proportion of cardiomyocytes in the heart (FIG. 13). Paradoxically, although our lineage-tracing findings unequivocally demonstrate that cKit$^+$ cardiomyocyte progenitors do not originate in the cardiac mesoderm (FIG. 11), studies in mouse embryonic (ES)- and induced pluripotent stem cells (iPSCs) have repeatedly documented that the generation of cKit$^+$ cardiomyocyte progenitors overlaps with the induction of the Nkx2.5$^+$ cardiac mesodermal progenitor lineage. Although these controversial findings previously led to the misidentification of cKit$^+$ progenitors as a subpopulation of the cardiac mesoderm, they prompted us to test whether the mechanisms controlling differentiation of cardiac mesoderm into myocardium also control cardiomyogenesis from CNC$^{kit}$.

First, to specifically address the relationship between CNC$^{kit}$ and the cKit$^+$/Nkx2.5$^+$ lineage purified from mouse ES and iPSCs-derived cardiac mesoderm, iPSCs from cKit$^{CreERT2}$/IRG adult tail-tip fibroblasts (iPSC$^{kit}$) were established. iPSC$^{kit}$ stably express DsRed with no leakage of EGFP (<30 passages). As with the cKit$^{CreERT2}$/IRG mice DsRed is irreversibly replaced by EGFP in iPSC$^{kit}$-derivatives upon Cre-mediated recombination, which occurs in response to treatment with 4-OH tamoxifen. Notably, EGFP epifluorescence in iPSC$^{kit}$ becomes visible ~48 h following treatment with 4-OH tamoxifen. Combined RNA-in situ hybridization and immunofluorescence analysis demonstrated the co-localization of Cre-recombinase with cKit. Thus, iPSC$^{kit}$ are suitable for in-vitro lineage tracing of cKit-expressing cells.

Figure 17:
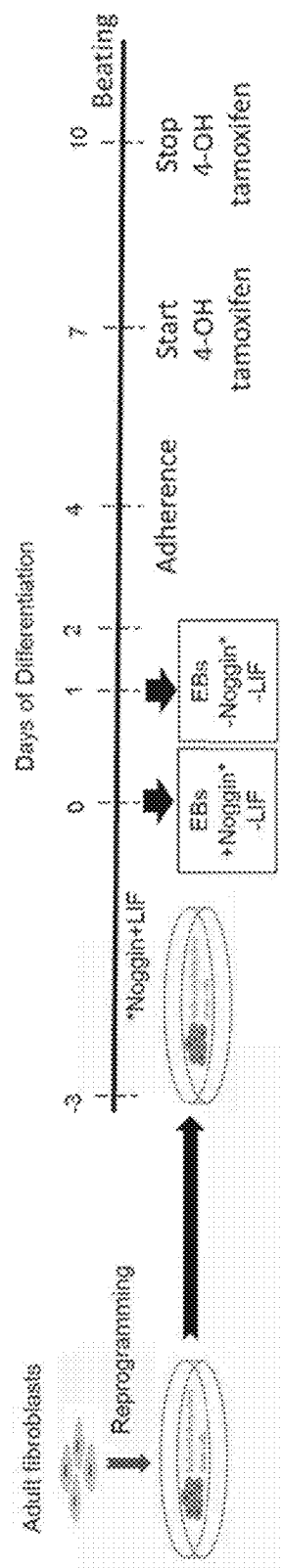
FIG. 17 shows transient inhibition of BMP signaling promotes the in-vitro generation of NCC$^{kit}$ from pluripotent stem cells; schematic description of the method to produce NCC$^{kit}$ from pluripotent stem cells.

Cardiomyocyte differentiation was induced by treatment of iPSC$^{kit}$-derived embryoid bodies (EB) with ascorbic acid as previously described (FIG. 17). Successful differentiation was reflected in the development of spontaneously contracting cardiomyocytes. To genetically trace whether any of the generated cardiomyocytes were progeny of cKit$^+$ progenitors, EBs were pulsed with 4-OH tamoxifen at selected time-points during differentiation and monitored the emergence of spontaneously beating EGFP$^+$ derivatives (FIG. 17). Indeed, EGFP$^+$ derivatives were detected in ~45% of the spontaneously beating EBs, confirming previous findings that mouse pluripotent stem cells can be consistently directed to generate cardiomyocytes via a cKit$^+$ cardiomyocyte progenitor lineage (data not shown).

Figure 18:
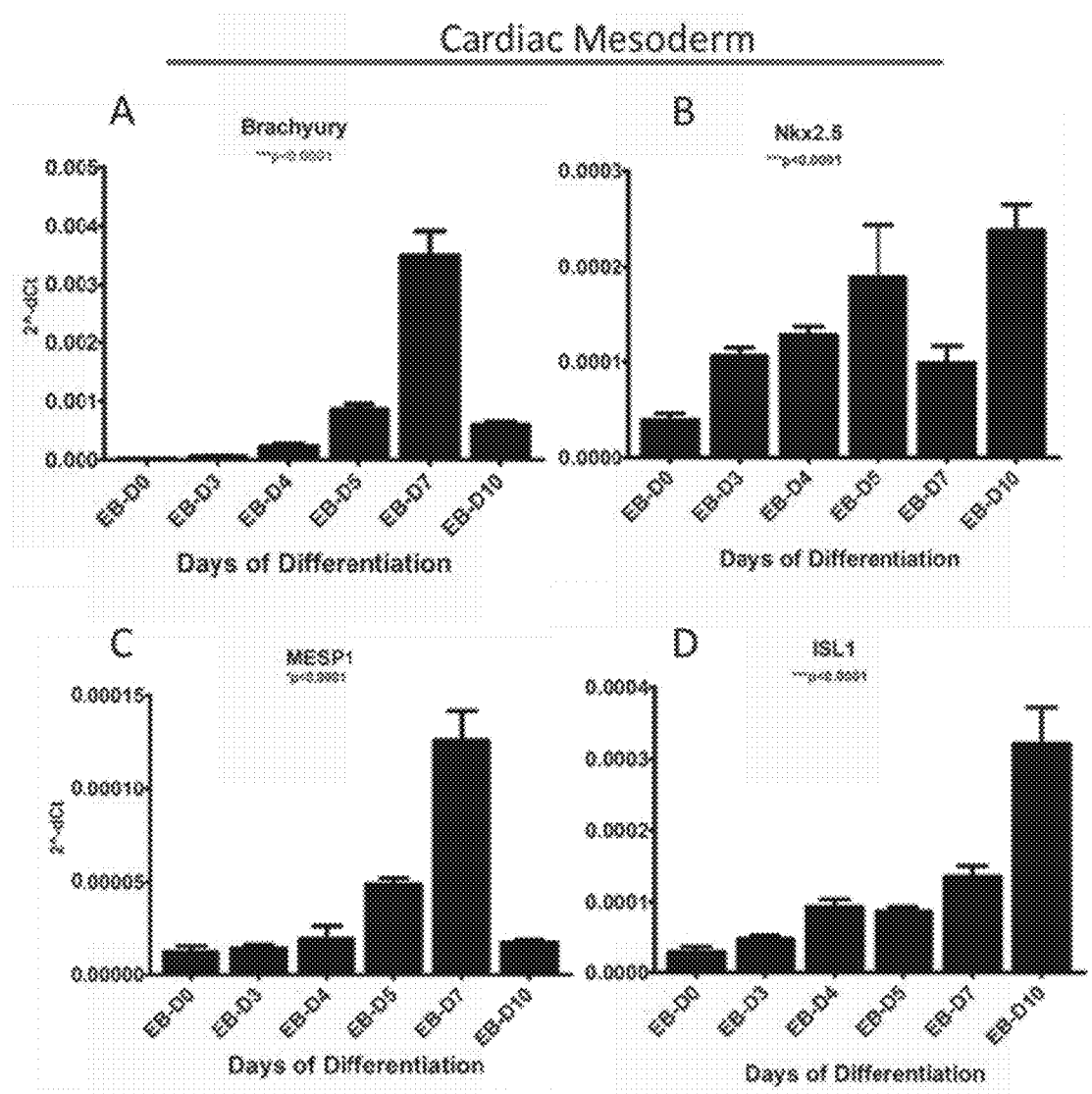
FIG. 18 shows gene expression analysis during the time course of iPSC differentiation into NCC$^{kit}$; Following the Brachyury- and Mesp1-mediated induction of cardiogenic mesoderm (A-D), noggin promotes the differentiation of pluripotent stem cells into the cardiac neural crest lineage, a subpopulation of which are the NCC$^{kit}$ (E-H).

However, although treatment with ascorbic acid enhances cardiogenesis in pluripotent stem cells, it is not a specific inducer of the cardiogenic mesoderm. Therefore, to elaborate the relationship between the iPSC$^{kit}$-derived presumptive cKit$^+$/Nkx2.5$^+$ cardiac mesodermal progenitor lineage and the CNC$^{kit}$, it was sought to genetically trace whether the cKit$^+$/Nkx2.5$^+$ lineage emerges following the directed differentiation of iPSC$^{kit}$ into cardiac mesoderm. Accordingly, iPSC$^{kit}$ were subjected to noggin-mediated antagonism of BMP signaling as previously described (FIG. 17). Gene-expression analysis at selected time-points demonstrated that the emergence of spontaneously beating cardiomyocytes preceded a transient induction of Brachyury and Mesp1, followed by a gradual increase in the expression of Nkx2.5 and Isl1; thus, showing that noggin specifies the generation of cardiomyocytes from cardiac mesodermal progenitors (data not shown). To genetically trace whether any of the generated cardiomyocytes were derived from the cKit$^+$/Nkx2.5$^+$ lineage, noggin-treated EBs were pulsed with 4-OH tamoxifen at selected time-points during their cardiogenic differentiation and monitored the emergence of spontaneously beating EGFP$^+$ derivatives (FIG. 17). Strikingly, similarly to treatment with ascorbic acid, treatment with noggin resulted in the generation of EGFP$^+$ cardiomyocytes. Confocal immunocytochemical analysis demonstrated that the EGFP$^+$ cardiac progenitors and cardiomyocytes co-expressed Nkx2.5, therefore confirming that noggin specifies the generation of cardiomyocytes, partly via the cKit$^+$/Nkx2.5$^+$ cardiogenic lineage (data not shown). However, since BMP signaling has also been reported to control generation of mouse neural crest cells and CNCs, as well as the induction of neural crest cells from human ES and iPSCs; and because our genetic lineage-tracing studies in the mouse embryos do not support the existence of the cKit$^+$/Nkx2.5$^+$ lineage within the cardiac mesoderm; it was sought to analyze whether, additionally to the cardiac mesoderm, treatment of iPSC$^{kit}$ with noggin may have promoted the generation of cardiac neural crest. Indeed, quantitative gene-expression analysis at selected time-points during their cardiogenic differentiation illustrated that, subsequently to the induction of Brachyury and Mesp1, and in parallel to the induction of Nkx2.5 and Isl1, noggin-treated iPSC$^{kit}$ underwent a dramatic upregulation in the expression of cKit, Wnt1, Snai2 and Pax3, and the heart-specific isoform of MITF, MITF-H (FIG. 18, Panels E-H). More importantly, noggin transiently repressed the expression of the epicardial progenitor cell markers WT1 and Tbx18, further supporting our lineage-tracing findings that cKit does not mark an epicardial progenitor cell lineage. Moreover, confocal immunocytochemical analysis of the EGFP$^+$ derivatives, illustrated that additionally to differentiating into cardiomyocytes and Nkx2.5 progenitors, iPSC-derived cKit progenitors gave rise to smooth muscle cells and Isl1$^+$ progenitors, while innervating the beating cardiomyocytes with neurofilament-M$^+$ and Tuj1$^+$ neurons (data not shown) Similar findings were found when noggin was replaced with the small molecule BMP antagonist dorsomorphin (FIG. 17). Thus, in line with our mouse genetic lineage-tracing studies, our in-vitro iPSC-based lineage tracing experiments confirm that cKit marks CNC progenitors with full cardiomyogenic capacity, and demonstrate that a transient inhibition of BMP signaling induces their differentiation into cardiomyocytes.

Our study elaborates a long-lasting controversy over the role of cKit as a marker of heart progenitors. By performing a genetic-linage tracing study and a high-resolution, intersectional genetic fate mapping analysis with a novel cKit$^{CreERT2/+}$ and Wnt1::Flpe4351 alleles in the developing mouse heart, we were able to determine that cKit marks cardiac progenitors of neural crest origin. We show that cKit$^+$ progenitors contribute a relatively small proportion of myocardium. However, by studying the mechanisms regulating their differentiation into cardiomyocytes in a mouse iPSCs model of cardiomyogenesis, our study suggests that the limited extent of myocardial contribution from CNC$^{kit}$ is not due to a minimal differentiation capacity as previously thought; rather, is regulated by the activity of BMP signaling in the heart which appears to be altered permanently, shortly after the induction of cardiac crescent and well-before the invasion of CNCs into the heart.

The lack of coronary vascular derivatives from cKit$^{CreERT2/+}$ expressing cells is in agreement with previous findings documenting a bipotential differentiation capacity of cKit$^+$ heart progenitors but comes in stark contrast with a recently reported genetic fate-map of cKit in the heart, using Kit$^{Cre/+}$ and Kit$^{mER-Cre-mER/+}$ alleles. These variations between the two genetic fate-mapping studies possibly reflect the differences underlying the targeting constructs and therefore different mutant versions of the coding sequences expressed by the targeted cKit alleles. Moreover, although CNC$^{kit}$ have capacity for endothelial and smooth muscle cell differentiation (data not shown) and therefore cannot exclude the existence of a vasculogenic cKit$^+$ cardiac lineage as observed by others, our findings are in line with recent endothelial lineage genetic-fate mapping analyses suggesting that the endothelial cells in the heart are unlikely to originate from a cKit$^+$ progenitor.

Last, our study identifies a novel signaling pathway that allows for the in-vitro directed differentiation of mouse pluripotent stem cells into the cardiac neural crest lineage, and demonstrate the full capacity of the mammalian CNC to derive cardiomyocytes under the proper environment. Together these findings, provide novel insights into the mechanisms regulating cardiomyogenesis in mammals, and enable the development of novel strategies for cell-based therapeutic strategies for heart repair.

Mice. cKit$^{CReERT2/+}$ mice were developed at the Medizinische Klinik and Poliklinik der Technischen Universität München, in Germany. The endogenous cKit locus was targeted by homologous recombination in embryonic stem (ES) cells as previously described for the Rosa26 locus. In brief, the targeting vector with the CreER$^{T2}$ cassette, an internal ribosome entry site and an frt-flanked neomycin resistance cassette was electroporated into 129S6 ES cells. Homologous recombination and single copy insertion was verified by Southern blot analysis and correctly targeted ES cells were injected into C57BL/6J blastocysts.

The previously established Wnt1-Cre, R26$^{tdTomato}$ IRG and R26R$^{Lacz}$ mouse lines were from Jackson Laboratories and details are available elsewhere. The Isl1$^{nLacz}$ mice were kindly provided by Dr. Sylvia Evans, at the University of California, San Diego, in USA, and have been previously described. The Isl1$^{nLacz}$ knock-in vector contains a LoxP-flanked nLacZ reporter gene followed by humanized *renilla* GFP. However, cells carrying this transgene do not express GFP, either before or after Cre-mediated excision of the floxed nLacZ reporter.

For lineage tracing experiments, cKit$^{CreERT2/+}$ mice were crossed to IRG or R26R$^{Lacz}$ Cre-reporters and embryos were studied at selected time points following tam-induced recombination. Wnt1-Cre mice were crossed to R26$^{tdTomato}$ and the resulting Wnt1-Cre/R26$^{tdTomato}$ progeny were studied at postnatal day 1. For the generation of embryos carrying a cKit$^{CreERT2}$/IRG:Isl1$^{nLacZ}$ genotype, male cKit$^{CreERT2}$/IRG mice were crossed to female Isl1$^{nLacz}$.

All animals were maintained in an AAALAC-approved animal facility at the University of Miami, Miller School of Medicine, and procedures were performed using IACUC-approved protocols according to NIH standards.

Genotyping.

Genomic DNA was isolated from mouse tail tips using the HotSHOT method, as previously described[50]. Genotyping was performed by PCR (Fermentas) according to manufacturer's instructions. The following primers were used: For cKit$^{CreERT2/+}$ CCTCCACCATAAGCCGAATA (SEQ ID NO: 1), CCTTCGAGGTGGTAGGCATG (SEQ ID NO: 2) and CCCCATTGTATGGGATCTGATC (SEQ ID NO: 3); for Isl1$^{nLacz}$: ACTATTTGCCACCTAGCCACAGCA (SEQ ID NO: 4) and GACAGTATCGGCCTCAGGAA (SEQ ID NO: 5). The Wnt1-Cre, R26$^{tdTomato}$ IRG and R26R$^{lacZ}$ genotyping protocols are available from Jackson laboratories. X-gal and immunofluorescence were also employed to validate PCR data. In addition, the white-spotting phenotype of cKit$^{CreERT2/+}$ was considered as the most reliable marker of their genotype.

Tamoxifen Injection.

For genetic fate-mapping, CreERT2 was activated by intraperitoneal injections of 100 µl of tamoxifen (Sigma), dissolved in peanut oil (Sigma) at a concentration of 20 mg/ml at desired time points, as previously described.

Briefly, for assessing the role of cKit in first or second heart-field progenitors, mice carrying cKit$^{CreERT2}$/IRG or cKit$^{CreERT2}$/R26R$^{LacZ}$ embryos received a daily injection of tamoxifen for 2 consecutive days, during E7.5-8.5. Embryos were harvested at E18.5. For assessing the expression of cKit in neural crest cells, mice carrying cKit$^{CreERT2}$/IRG or cKit$^{CreERT2}$/R26R$^{LacZ}$ embryos received a daily injection of tamoxifen for 3 consecutive days, either during E9.5-11.5 or during E10.5-12.5. Embryos were harvested at E18.5. To trace the co-expression of Isl1-driven nLacZ and cKit$^{CreERT2}$/IRG-driven EGFP in cKit$^{CreERT2}$/IRG:Isl1$^{nLacZ}$ embryos, microscopic analysis was performed within 24 h after the last injection of tam. This strategy allowed us to detect cells in which Cre-mediated recombination was induced for a period of time that was sufficient to report expression of EGFP before expression of nLacZ disappear.

For ex-vivo tissue culture experiments, 2-day old cKit$^{CreERT2}$/IRG neonates were administered a single subcutaneous injection of 50 µl of tamoxifen and hearts were harvested after 24 h. This strategy allowed clonal labeling of cardiac CNC$^{kit}$.

Mouse Embryo Dissections.

Females with a vaginal plug were considered at E0.5, as previously described. Embryos at different time points were harvested in ice-cold Hank's Balanced Salt solution (HBSS, Gibco). For E12.5 and E18.5 embryos carrying the cKit$^{CreERT2}$/IRG alleles, live-tissue imaging was performed immediately after dissection under a fluorescence microscope (Olympus) and EGFP and DsRed epifluorescence were photodocumented. Samples were then fixed for 1-1½ h in 4% PFA (EMS) at room temperature followed by overnight incubation in 30% sucrose (Calbiochem) at 4° C. Next day, samples were embedded in OCT (EMS) and flash-frozen in liquid nitrogen. Cryosectioning was performed as previously described.

For cKit immunohistochemical analyses, E12.5-E14.5 wild-type mouse embryos were harvested and fixed overnight in 10% buffered formalin. Next day, they were embedded in paraffin and processed for immunohistochemistry as previously described.

X-Gal Histochemistry.

X-gal histochemistry was performed using a β-galactosidase staining kit (Invitrogen) in fixed intact mouse embryonic hearts or embryos carrying the cKit$^{CreERT2}$/R26R$^{LacZ}$ or Isl1$^{nLacZ}$ alleles, as well as their respective littermates, as described before. Briefly, samples were incubated overnight in x-gal solution (Invitrogen) at 37° C. The next day, x-gal was washed away with PBS, samples were photodocumented under a light microscope (Nikon) and incubated overnight in 30% sucrose at 4° C. Fixed tissues were then embedded in OCT and processed for cryosectioning. In some instances of cKit$^{CreERT2}$/IRG:Isl1$^{nLacZ}$ embryos, x-gal was performed after cryosectioning, following EGFP immunostaining.

Immunofluorescence Confocal Microscopy.

For cryosections, 10 µm-thick samples were post-fixed for 10 min with 4% PFA. For paraffin-embedded tissues, 4-5 µm-thick tissue sections were deparaffinized and rehydrated as previously described. Antigen unmasking was performed by microwaving the slides for 2×10 min in citrate buffer Solution, pH=6 (Dako, Carpenteria, Calif.). Sections were then blocked for 1 h at RT with 10% normal donkey serum (Chemicon International Inc, Temecula, Calif.), followed by overnight incubation at 4° C. with the primary antibody.

The following antibodies were used: cKit (DAKO, ebiosciences and R&D), EGFP (Abcam, Ayes, Invitrogen), beta-galactosidase (Invitrogen), Connexin-43, KDR, MITF, PECAM1, α-smooth muscle actin (Sigma), Anti-Smooth Muscle Myosin Heavy Chain (SM1; Kamiyau Biomedical), cardiac troponin-I, Calponin, tropomyosin, Tyrosinase (Abcam), cardiac myosin light chain-2v, Neurofilament-M, BFABP, Wnt1 (Novus Biologicals), Nkx2.5 (R&D), GATA-4 (Santa Cruz Biotechnologies), Isl-1 (40.2D6, Developmental Studies Hybridoma Bank, IA), Factor VIII-related antigen (Biocare Medical), Tuj1 (Covance). Subsequently, the antibodies were visualized by incubating the sections for 1 h at 37° C. with FITC, Cy3 and Cy5-conjugated F(ab')$_2$ fragments of affinity-purified secondary antibodies (Jackson Immunoresearch). For MITF and SM1, tyramide signal amplification was employed according to manufacturer's instructions (Perkin Elmer). Slides were counterstained with DAPI, mounted with ProLong Antifade Gold reagent (Invitrogen,) and stored at 4° C. until further examination. Microscopic evaluations and image acquisitions were performed with a Zeiss LSM-710 Confocal Microscope (Carl Zeiss MicroImaging, Inc. Thornwood, N.Y.). The Zeiss ZEN software (version 2009, Carl Zeiss Imaging Solutions, GmbH) was used.

Multiplex Fluorescence In Situ Hybridization (RNA-ISH).

Single-cell gene expression analyses was performed using a multiplex RNA-ISH assay (Quantigene viewRNA kit, Panomics), according to manufacturers' instructions. Briefly, cytospins of CNC$^{kit}$ were fixed for 30 min with 4% paraformaldehyde and digested with protease solution for 10 min at 37° C. Probes against the human cKit (NM_000222.2), Isl1 (NM_002202.2), NKX2-5 (NM_004387.3), GATA4 (NM_002052.3) and GAPDH were applied and hybridized overnight in a hybridizer (Dako).

Statistical Analysis.

For genetic lineage-tracing experiments, we estimate that in order to detect a minimum difference of 30 cardiomyocytic derivatives per cryosection between groups, with an expected standard deviation of ±6 cardiomyocytes with a power of 90% and a 0.05 alpha-level, at least two embryos per group are necessary. Here, we used 10 embryos to perform genetic lineage tracing of cKit during E7.5-E8.5, 12 embryos during E9.5-12.5 and 6 embryos of the ckit$^{CreERT2}$/IRG:Isl1$^{nLacZ}$ genotype. Randomization and blinding were not applicable for this animal study. Statistical analyses were performed using GraphPad Prism version 5.00 for Windows. A two-way repeated measures ANOVA followed by Bonferroni posthoc tests, was employed for comparing in-vitro quantification data of EGFP$^{(+)}$ cells. All data met the assumptions of the tests. A p<0.05 was considered statistically significant. All values are reported as mean±SEM.

What is claimed is:

1. A method of producing cKit-positive, Mesp1-negative, and Nkx2.5-positive cardiac neural crest cells comprising:
   culturing a plurality of stem cells, wherein the plurality of stem cells are induced pluripotent stem cells, with noggin and leukemia inhibitory factor;
   culturing the plurality of stem cells with noggin, thereby forming three-dimensional aggregates of the plurality of stem cells; and
   culturing the plurality of stem cells in cardiac neural crest differentiation medium, wherein the cardiac neural crest differentiation medium comprises fetal bovine serum and a growth medium, to form cardiac neural crest cells; and
   isolating the cardiac neural crest cells that are cKit-positive Nkx2.5-positive, and Mesp1-negative,
   wherein the growth medium is Iscove's Modified Dulbecco's Medium (IMDM), Dulbecco's Modified Eagle Medium (DMEM), Minimum Essential Medium (MEM), Roswell Park Memorial Institute 1640 Medium, F10 Nutrient Mixture, Ham's F12 Nutrient Mixture, Media 199, or any combination thereof.

2. The method of claim 1, further comprising treating a cardiac injury in a subject in need thereof comprising administering a therapeutically effective amount of a pharmaceutical composition comprising the produced cardiac neural crest cells.

3. The method of claim 2, wherein the cardiac injury is a cardiac injury caused by myocardial infarction, heart failure, cardiomyopathy, congenital heart disease, nutritional diseases, ischemic or non-ischemic cardiomyopathy, hypertensive cardiomyopathy, valvular cardiomyopathy, inflammatory cardiomyopathy, cardiomyopathy secondary to a systemic metabolic disease, alcoholic cardiomyopathy, diabetic cardiomyopathy, restrictive cardiomyopathy, and combinations thereof.

4. The method of claim 2, wherein the pharmaceutical composition has about 50% by weight to about 100% by weight cardiac neural crest cells.

5. The method of claim 2, wherein the pharmaceutical composition has about 50% by weight cardiac neural crest cells.

6. The method of claim 2, wherein the pharmaceutical composition has about $1\times10^6$ cardiac neural crest cells.

7. The method of claim 1, wherein the noggin in the step of culturing a plurality of stem cells with noggin and leukemia inhibitory factor is at a concentration of 150 ng/ml.

8. The method of claim 1, wherein the leukemia inhibitory factor in the step of culturing a plurality of stem cells with noggin and leukemia inhibitory factor is at a concentration of 2000 units/ml.

9. The method of claim 1, further comprising contacting tamoxifen to the stem cells.

* * * * *

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence

```
<220> FEATURE:
<223> OTHER INFORMATION: synthetic sequence

<400> SEQUENCE: 1
cctccaccat aagccgaata                                        20

<210> SEQ ID NO 2
<211> LENGTH: 20
<212> TYPE: DNA
<213> ORGANISM: Artificial Sequence
<220> FEATURE:
<223> OTHER INFORMATION: synthetic sequence

<400> SEQUENCE: 2
ccttcgaggt ggtaggcatg                                        20

<210> SEQ ID NO 3
<211> LENGTH: 22
<212> TYPE: DNA
<213> ORGANISM: Artificial Sequence
<220> FEATURE:
<223> OTHER INFORMATION: synthetic sequence

<400> SEQUENCE: 3
ccccattgta tgggatctga tc                                     22

<210> SEQ ID NO 4
<211> LENGTH: 24
<212> TYPE: DNA
<213> ORGANISM: Artificial Sequence
<220> FEATURE:
<223> OTHER INFORMATION: synthetic sequence

<400> SEQUENCE: 4
actatttgcc acctagccac agca                                   24

<210> SEQ ID NO 5
<211> LENGTH: 20
<212> TYPE: DNA
<213> ORGANISM: Artificial Sequence
<220> FEATURE:
<223> OTHER INFORMATION: synthetic sequence

<400> SEQUENCE: 5
gacagtatcg gcctcaggaa                                        20
```